(12) United States Patent
Madabhushi et al.

(10) Patent No.: US 10,441,215 B2
(45) Date of Patent: Oct. 15, 2019

(54) PREDICTING IMMUNOTHERAPY RESPONSE IN NON-SMALL CELL LUNG CANCER WITH SERIAL QUANTITATIVE VESSEL TORTUOSITY

(71) Applicant: Case Western Reserve University, Cleveland, OH (US)

(72) Inventors: Anant Madabhushi, Shaker Heights, OH (US); Yuanqi Xie, Cleveland, OH (US); Vamsidhar Velcheti, Pepper Pike, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 15/893,086

(22) Filed: Feb. 9, 2018

(65) Prior Publication Data
US 2018/0242906 A1    Aug. 30, 2018

Related U.S. Application Data

(60) Provisional application No. 62/464,007, filed on Feb. 27, 2017.

(51) Int. Cl.
*G06K 9/00* (2006.01)
*A61B 5/00* (2006.01)
(Continued)

(52) U.S. Cl.
CPC ........ *A61B 5/4839* (2013.01); *A61B 5/02007* (2013.01); *A61B 5/4848* (2013.01);
(Continued)

(58) Field of Classification Search
CPC combination set(s) only.
See application file for complete search history.

(56) References Cited

U.S. PATENT DOCUMENTS

| 5,762,921 A * | 6/1998 | Vehar ................ A61K 38/06 424/158.1 |
| 2010/0254589 A1* | 10/2010 | Gallagher ............ G06K 9/0014 382/133 |

(Continued)

OTHER PUBLICATIONS

U.S. Appl. No. 15/853,133, filed Dec. 22, 2017.
Non Final Office Action dated Jul. 23, 2019 in connection with U.S. Appl. No. 15/853,133.

*Primary Examiner* — Alex Kok S Liew
(74) *Attorney, Agent, or Firm* — Eschweiler & Potashnik, LLC

(57) ABSTRACT

One embodiment includes an image acquisition circuit that accesses a pre-treatment and a post-treatment image of a region of tissue demonstrating non-small cell lung cancer (NSCLC), a segmentation and registration circuit that annotates the tumor represented in the images, and that registers the pre-treatment image with the post-treatment image; a feature extraction circuit that selects a set of pre-treatment and a set of post-treatment quantitative vessel tortuosity (QVT) features from the registered image; a delta-QVT circuit that generates a set of delta-QVT features by computing a difference between the set of post-treatment QVT features and the set of pre-treatment QVT features; and a classification circuit that generates a probability that the region of tissue will respond to immunotherapy based on the difference, and that classifies the region of tissue as a responder or non-responder. Embodiments may generate an immunotherapy treatment plan based on the classification.

31 Claims, 8 Drawing Sheets

(51) Int. Cl.

| | | |
|---|---|---|
| *G06T 7/11* | (2017.01) | |
| *G06T 7/33* | (2017.01) | |
| *G06T 7/00* | (2017.01) | |
| *G06K 9/62* | (2006.01) | |
| *G16H 30/40* | (2018.01) | |
| *A61B 6/00* | (2006.01) | |
| *A61K 49/00* | (2006.01) | |
| *G06K 9/46* | (2006.01) | |
| *A61B 5/02* | (2006.01) | |
| *G06T 7/174* | (2017.01) | |
| *A61B 6/03* | (2006.01) | |
| *A61B 5/055* | (2006.01) | |

(52) U.S. Cl.
CPC .............. *A61B 5/7267* (2013.01); *A61B 6/50* (2013.01); *A61K 49/0004* (2013.01); *G06K 9/46* (2013.01); *G06K 9/6256* (2013.01); *G06K 9/6267* (2013.01); *G06K 9/6269* (2013.01); *G06K 9/6277* (2013.01); *G06K 9/6284* (2013.01); *G06T 7/0014* (2013.01); *G06T 7/0016* (2013.01); *G06T 7/11* (2017.01); *G06T 7/174* (2017.01); *G06T 7/337* (2017.01); *G16H 30/40* (2018.01); *A61B 5/055* (2013.01); *A61B 5/4842* (2013.01); *A61B 5/7264* (2013.01); *A61B 6/032* (2013.01); *G06K 2209/05* (2013.01); *G06T 2200/04* (2013.01); *G06T 2207/10081* (2013.01); *G06T 2207/20076* (2013.01); *G06T 2207/20081* (2013.01); *G06T 2207/20084* (2013.01); *G06T 2207/30024* (2013.01); *G06T 2207/30061* (2013.01); *G06T 2207/30064* (2013.01); *G06T 2207/30096* (2013.01); *G06T 2207/30101* (2013.01)

(56) References Cited

U.S. PATENT DOCUMENTS

| | | | |
|---|---|---|---|
| 2010/0303714 A1* | 12/2010 | Kirn | C12N 15/86 424/1.11 |
| 2011/0181614 A1* | 7/2011 | Chang | G06T 7/0012 345/595 |
| 2011/0318430 A1* | 12/2011 | Meruelo | A61K 31/337 424/649 |
| 2013/0329973 A1* | 12/2013 | Cao | A61B 5/0033 382/128 |
| 2015/0254840 A1 | 9/2015 | Madabhushi | |
| 2016/0220711 A1* | 8/2016 | DeMore | C07K 16/18 |

* cited by examiner

PREDICTING IMMUNOTHERAPY RESPONSE IN NON-SMALL CELL LUNG CANCER WITH SERIAL QUANTITATIVE VESSEL TORTUOSITY

CROSS REFERENCE TO RELATED APPLICATIONS

This application claims the benefit of U.S. Provisional Application 62/464,007 filed Feb. 27, 2017.

BACKGROUND

PD-L1 inhibitors are a group of drugs that inhibit the interaction between programmed death-ligand 1 (PD-L1) with its receptor, programmed cell death protein 1 (PD-1). This pathway, once activated, is a mechanism for tumor escape by T-cell exhaustion. Inhibition of this pathway is one approach to treating cancer. Nivolumab, a human IgG4 anti-PD-1 monoclonal antibody, works as an immune checkpoint inhibitor that blocks this pathway. Nivolumab is used to treat chemotherapy refractory advanced non-small cell lung cancer (NSCLC). As immunotherapy agents, such as nivolumab, become more widely used in treating NSCLC, medical practitioners face a challenge in the evaluation of the clinical efficiency of such immunotherapy agents.

There are no standard guidelines for evaluating response to treatment with PD-L1 checkpoint inhibitors such as nivolumab. In clinical practice, conventional radiological tools, including the Response Evaluation Criteria in Solid Tumors (RECIST), have been employed. The RECIST criteria consider a significant increase in the size of tumor lesions and the development of new lesions to be unequivocal disease progression. Conventional approaches such as the RECIST criteria are used as operational thresholds that mandate the cessation of current therapy and the initiation of an alternate therapeutic regime. However, these conventional approaches that take into account the widest diameter of the tumor have underestimated the benefit of therapy to patients because of the increase in tumor dimensions in patients who otherwise responded favorably to the treatment.

Such patients may be referred to as "pseudoprogressors". Some patients respond to immunotherapy with tumor shrinkage or stable disease and are thus more likely to be accurately characterized by the RECIST criteria. However, pseudoprogressors may exhibit distinct immune-related patterns of response, including new lesions associated with edema, infiltrates of immune cells, and transient increases in baseline tumor lesions. Delayed clinical responses to immunotherapeutic agents may also be observed, resulting in an initial increase in total tumor burden which is then followed by tumor regression. These pseudoprogressor findings are misclassified by conventional approaches as progressive disease, which may lead to poor patient outcomes because treatment that would be helpful is mischaracterized as ineffective and then terminated. Additionally, positron emission tomography (PET) also shows false positives because of the activation of T-cells against cancer cells, which may lead to uptake of fluorodeoxyglucose (FDG). Thus, conventional approaches to predicting patient response to immunotherapy and determining courses of treatment are not optimal.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
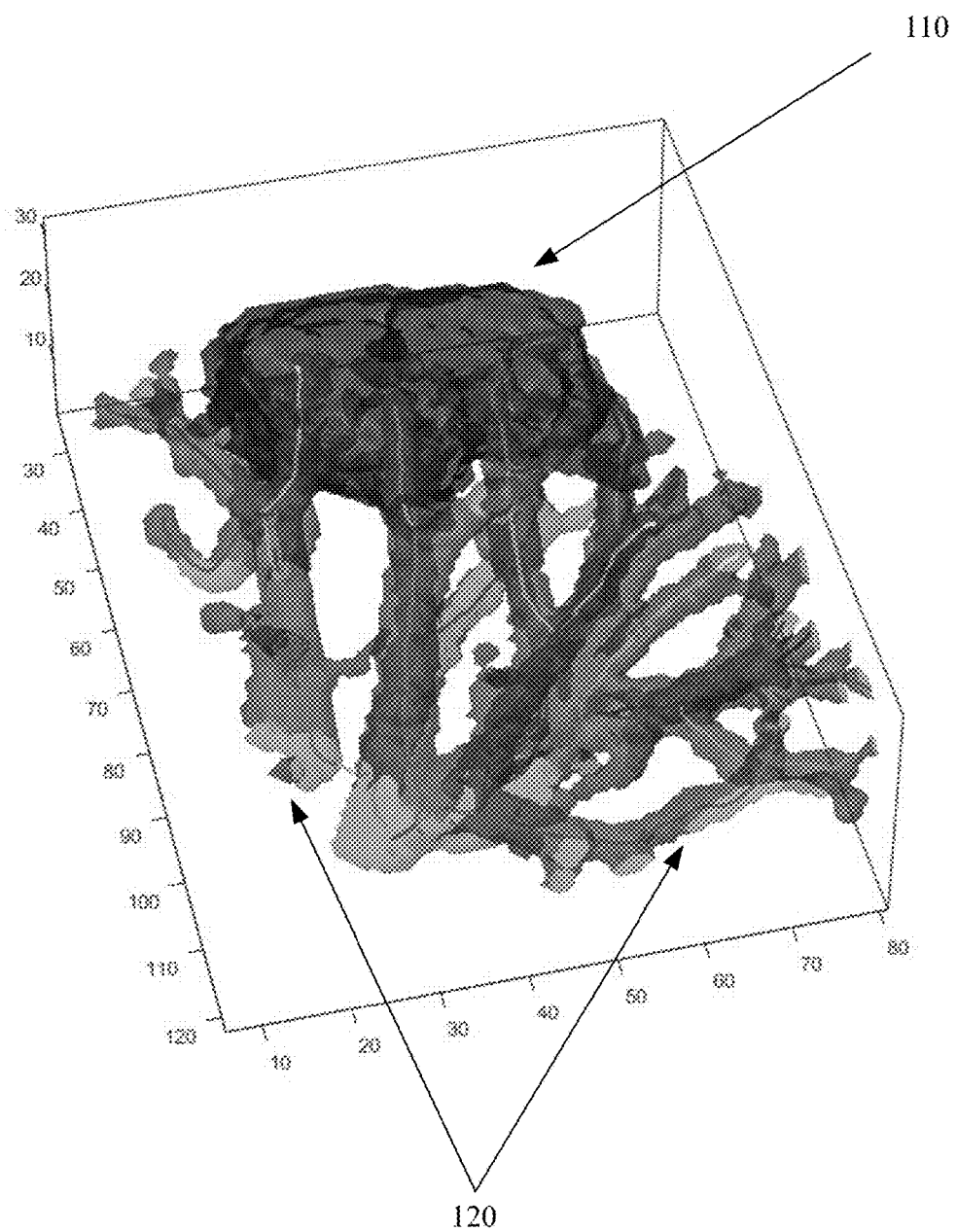
FIG. 1 illustrates an example three dimensional (3D) segmented vasculature.

Embodiments described herein use computer extracted measurements of quantitative imaging features that significantly and differentially change post treatment between NSCLC patients who do and do not respond to immunotherapy to predict patient response to immunotherapy. While one embodiment described herein predicts NSCLC patient response to nivolumab immunotherapy, other embodiments may predict patient response to other types of immunotherapy, or for other types of cancer, including breast cancer, head and neck cancer, bladder cancer, prostate cancer, rectal cancer, melanoma, brain cancer including Glioblastoma, or other types of cancer. Example embodiments directly transform a CT image of lung tissue into a probability of a patient-level response to immunotherapy, and generate an NCSLC immunotherapy treatment plan based on the probability of response. Unlike conventional approaches that suffer from less than optimal inter and intra-rater reliability, example methods and apparatus automatically and reproducibly quantify the probability that a patient will respond to immunotherapy. Example methods and apparatus use automated computational quantitative vessel tortuosity (QVT) image analysis to generate a patient-level prediction of response to immunotherapy based on differences between sub-visual features extracted from baseline pre-treatment CT imagery and post-treatment CT imagery with a receiver operating characteristic area under the curve (AUC) of at least 0.79. The sub-visual features extracted from CT imagery are more than volumetric measurements, and characterize the biology of the disease. These sub-visual characteristics thus serve, in one embodiment, as a biomarker to predict treatment response and to visualize disease processes in a non-invasive manner. Example methods and apparatus are more accurate and reliable in predicting patient response to immunotherapy than conventional computer assisted approaches, and are also more accurate and reliable than expert human pathologists.

Embodiments described herein may train, test, and employ a machine learning classifier, including a support vector machine (SVM), to predict patient response to immunotherapy, based on features extracted from digitized CT images of lung tissue. Example methods and apparatus automatically and reproducibly predict patient response to immunotherapy based on baseline and post-treatment imagery because the computed difference in features between the baseline and post-treatment CT images, and the machine learning classifier, are deterministic and will repeatedly produce the same classification on the same input sample. This is in contrast to human experts that exhibit inter-expert and intra-expert variances. Automated analysis and grading of baseline and post-treatment CT imagery as described herein may further be employed as an objective second read of human radiologists or oncologists to improve NSCLC treatment, including the application of immunotherapy. Example embodiments support personalized medicine and precision medicine initiatives to enhance the targeting of therapeutics based on the deeper understanding of disease mechanisms and their manifestations within individual patients provided by example embodiments.

The vasculature associated with malignancy is abnormally shaped. Dysregulation of angiogenesis is a hallmark of solid tumors. An imbalance of pre-angiogenic and anti-angiogenic signaling within tumors creates an abnormal vascular network. This abnormal vascular network may be characterized by dilated, tortuous, or hyperpermeable vessels. These abnormalities and the resultant microenvironment fuel tumor progression. These abnormalities and the resultant microenvironment also lead to a reduction in the efficacy of chemotherapy and immunotherapy.

Malignancy makes regional changes to vessel shape and tortuosity. Tortuosity abnormalities appear during the tumor development process and affect initially healthy vessels which are spread beyond the confines of the tumor or tumor margins. The tortuosity of vessels in a tumor or nodule, or in the tumor's neighborhood (e.g. perinodular zone) contains prognostic information that facilitates discriminating responders from non-responders. The tortuosity of vessels associated with a tumor is also associated with underlying gene-expression patterns. Thus, the tortuosity of vessels in a tumor, nodule, or other region of tissue (e.g. perinodular zone) associated with a tumor or nodule may be used by example methods and apparatus to facilitate supporting decisions made to predict patient response to immunotherapy. Tortuosity features capture vascular curvature, branching statistics, and tortuosity characteristics of vessels associated with the tumor or nodule. Tortuosity features, compared to other features employed by conventional approaches, are intensity invariant, and do not exhibit sensitivity to imaging parameters such as scale or resolution that makes conventional approaches sub-optimal. Example embodiments thus facilitate the classification of tumors represented in radiological images that may be acquired on different machines, using different imaging parameters, and from across different institutions. Since a more accurate distinction is made, example apparatus and methods thus predict patient outcomes in a more consistent and reproducible manner than conventional approaches.

In one embodiment, CT images were acquired from a cohort of patients who were treated with nivolumab over a 34 month period. All patients in the cohort underwent baseline, pre-treatment CT imaging before starting treatment with nivolumab. For a patient, after four doses of nivolumab, where each dose was administered two weeks apart, a follow up CT scan was acquired at each two-week interval. In this embodiment, fifty (50) patients in the cohort who underwent treatment with nivolumab were divided into a group of responders and a group of non-responders. Patients who did not receive nivolumab treatment after two cycles due to lack of response or to disease progression were classified as non-responders. Disease progression in this embodiment is defined as at least a 20% increase in the sum of diameters of target lesions, as per RECIST v1.1. Patients who experienced radiological response, including complete response (CR), and non-CR/non-progressive disease (PD), as per RECIST v1.1, or stable disease, as per RECIST v.1.1, or who experienced clinical improvement, were classified as responders. In this embodiment, CR is defined as the disappearance of all non-target lesions and normalization of tumor marker level. Non-CR/non-PD is defined as persistence of one or more non-target lesions or maintenance of tumor marker level above standard limits. In this embodiment, the cohort was divided into a training cohort of 25 patients, and a testing cohort of 25 patients that was held out and used as a blinded validation set.

In this embodiment, lung nodules or tumors represented in the pre-treatment CT images and post-treatment CT images are annotated using three dimensional (3D) Slicer software by an expert human radiologist. Annotating a lung nodule may include segmenting the nodule from the background of the image. In another embodiment, lung nodules may be annotated using other techniques, included automated segmentation techniques. Post-treatment CT images were then co-registered to pre-treatment CT images. In one embodiment, the post-treatment images were co-registered to the pre-treatment CT images using an Elastix registration tool, while in another embodiment, other registration techniques may be employed. Co-registration ensures that acquired CT scans for a patient at different time points are registered to the baseline CT image, which facilitates more accurate comparison of tortuosity features. In this embodiment, affine registration is employed, while in other embodiments, other registration techniques may be used. Registration may be manually adjusted by an expert human radiologist, or may be adjusted automatically.

Example embodiments extract QVT features from the registered baseline pre-treatment CT image and the post-treatment CT image or images. A CT image has a plurality of voxels. A voxel has an intensity value. In this embodiment, QVT features are quantitative image features generated from information extracted from voxels in the CT imagery. QVT features may be used for quantitative prediction or prognostic purposes in cancer diagnostics or in generating a cancer treatment plan for a patient. QVT features include a torsion standard deviation feature, a curvature standard deviation feature, a number of branches feature, or other tortuosity or branching features or statistical measures of such features.

Embodiments described herein select QVT features that achieve at least a threshold level of discriminability in characterizing a region of tissue as a responder or non-responder. Embodiments described herein may also select QVT features based on a level of stability between baseline pre-treatment imagery and post-treatment imagery. For example, embodiments described herein may select QVT features based on a threshold level of reliability and a threshold level of reproducibility between baseline pre-treatment imagery and post-treatment imagery. In one embodiment, QVT features include a total of 35 features automatically extracted from annotated nodules. The QVT features include a torsion standard deviation feature, a curvature standard deviation feature, a number of branches feature, or other tortuosity or branching feature. Extracted QVT features are then normalized to adjust values to a notionally common scale between −1 and 1. Embodiments described herein further compute a percent difference of feature values between pre-treatment imagery and post-treatment imagery, and select these serial (e.g. delta) QVT features that are highly discriminative between responders and non-responders based on the computed difference.

Embodiments described herein may select QVT features using a feature selection approach selected from among different feature selection approaches. Different feature selection approaches include a T-test score method, a Wilcoxon rank sum method, or a minimum redundancy maximum relevancy (mRMR) approach. A first feature selection approach may select different QVT features from the same image than a second, different feature selection approach. For example, an mRMR feature selection approach may select a torsion standard deviation feature, while a different feature selection approach may select different tortuosity features. In a preferred embodiment, an mRMR feature selection approach is employed.

Embodiments described herein employ a machine learning classifier to characterize a region of tissue as a responder or non-responder using the selected delta-QVT features. The machine learning classifier may be a supervised learning classifier which learns from labeled training samples. Labeled training samples may include the images acquired from the training cohort of 25 patients, and the testing cohort of 25 patients that was used as a blinded validation set.

Embodiments described herein may identify and remove outlier cases from the training and testing cohorts. Removing outlier cases facilitates more effectively training the machine learning classifier to accurately characterize a region of tissue as a responder or non-responder. In one embodiment, selecting outliers involves three steps. In a first unsupervised clustering step, the top six most discriminative features are selected from the images acquired from the training cohort of 25 patients, and the testing cohort of 25 patients. The top three of those top six features are used to generate two 3D plots: a first 3D plot of the training cohort of 25 patients and a second, different 3D plot the testing cohort of 25 patients. In a second step, in the first 3D plot and the second 3D plot, the distance between each two samples is calculated. In one embodiment, an L2 norm is calculated to compute a distance between the delta tortuosity measurements. In a third step, samples that have relatively larger distances are selected as the outliers. For example, in one embodiment, a threshold based on assumptions of normality and 95% confidence intervals is used to select outliers. In this embodiment, any sample that falls outside 2 standard deviations of the mean value is deemed an outlier and eliminated. Training the machine learning classifier with a training dataset that has the outliers removed results in improved accuracy of classification compared to approaches that do not remove outliers. Furthermore, reducing the number of samples used to train the classifier by selectively removing outliers, while improving accuracy, also increases the speed with which the classifier may be trained, which improves the performance of a computer, processor, or computer-related technology in which example embodiments are implemented. While in this example, eliminating outliers includes three steps, in another embodiment, outliers may be eliminated using other, different techniques or numbers of steps.

The machine learning classifier may be a discriminant analysis (DA) machine learning classifier, a nearest neighbor (NN) machine learning classifier, a random forest (RF) machine learning classifier, or a support vector machine (SVM). A DA machine learning classifier may be a linear discriminant analysis (LDA) classifier, or a quadratic discriminant analysis (QDA) classifier. In one embodiment, the SVM classifier may have three kernels, including a linear kernel, a radial basis function (RBF) kernel, and a polynomial kernel. In another embodiment, the machine learning classifier may employ a convolutional neural network (CNN).

Embodiments described herein select QVT features based on a level of stability between baseline pre-treatment imagery and post-treatment imagery using a QVT feature concordance approach. Example embodiments may employ a concordance correlation coefficient (CCC) to evaluate the reproducibility and reliability between features extracted from a pre-treatment CT image and a post-treatment CT image acquired from the same patient. In one embodiment, a CCC value of 0.8 is used as a threshold to assess reproducibility of the radiomic feature. A QVT feature with a CCC value greater than 0.8 is considered a reproducible feature. To further ensure stability of QVT features, after classification of the training set, the six top ranked features were selected. Using the Reference Image Database to Evaluate Therapy Response (RIDER) dataset of CT images of patients demonstrating NSCLC, the CCC value for the six top ranked features may be calculated. While a CCC value of 0.8 is described, other CCC values may be employed, and other conditions, such as a CCC value greater than or equal to (>=) the threshold value may be employed. By selecting QVT features based, in part, on the stability of the feature as represented by the CCC value, example embodiments improve the reproducibility and reliability of tissue classification by systems, apparatus, processors, computers, and methods described herein compared to conventional approaches that do not consider feature stability.

Figure 3:
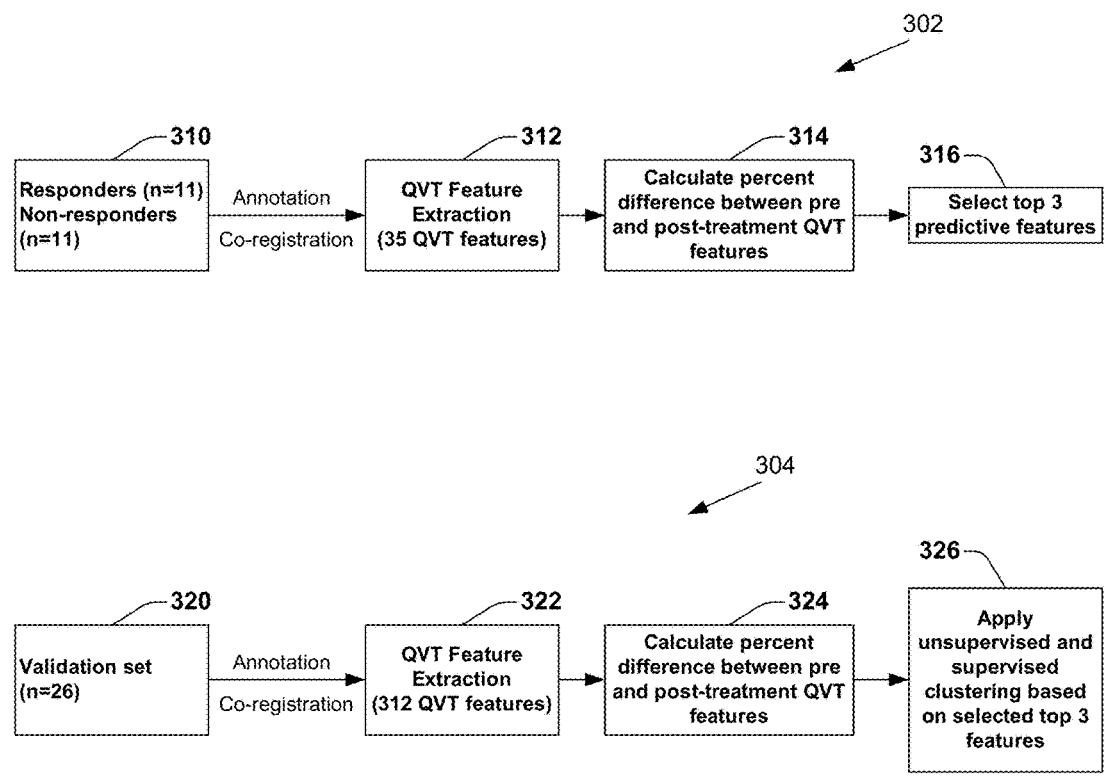
FIG. 3 is a schematic overview of a workflow to train and test a machine learning classifier to predict response to immunotherapy based on serial quantitative vessel tortuosity (QVT) features.

FIG. 3 is a schematic overview of a workflow to train and test a machine learning classifier suitable for use by embodiments described herein. FIG. 3 illustrates a first workflow 302 associated with a learning or training set of patients demonstrating NSCLC, and a second workflow 304 associated with a validation or testing set of patients demonstrating NSCLC that is disjoint from the training set. FIG. 3 illustrates, at 310, a training cohort of 22 patients including 11 responders and 11 non-responders. While 11 responders and 11 non-responders are illustrated in this example, other different numbers of responders and non-responders may be employed. The size of the training cohort may be determined based on available imagery, or may be based on an optimization of training effect or training time. Pre-treatment CT images and post-treatment CT images of a region of tissue demonstrating NSCLC are acquired of each member of the training cohort 310. A lung nodule or tumor represented in a pre-treatment CT image and in the corresponding post-treatment image is annotated, and the pre-treatment CT image is registered with the post-treatment CT image. At 312, a set of QVT features is extracted from the registered images. In this example, 35 QVT features are extracted. At 314, a percent difference is computed between features extracted from the pre-treatment and corresponding post-treatment images to generate a set of delta-QVT features. At 316, the top 6 features predictive of response to immunotherapy are selected. While the top 6 features are selected in this example, other different numbers of features (e.g., 3, 4, 5, or 7) may be selected.

FIG. 3 further illustrates second workflow 304 for testing a machine learning classifier using a testing or validation cohort 320 of 26 patients demonstrating NSCLC. Pre-treatment CT images and post-treatment CT images of a region of tissue demonstrating NSCLC are acquired from members of the validation cohort 320. A lung nodule or tumor represented in a pre-treatment CT image and in the corresponding post-treatment CT image is annotated, and the pre-treatment CT image is registered with the post-treatment CT image. At 322, a set of QVT features is extracted from the registered images. At 324, a percent difference is computed between features extracted from the pre-treatment and corresponding post-treatment images to generate a set of delta-QVT features. While in this example, a percent difference is computed, in other embodiments, other measures of difference may be employed to generate the set of delta-QVT features. For example, embodiments described herein may scale the delta-QVT features with respect to either the pre-treatment or post-treatment QVT feature measurements. The set of delta-QVT features selected is based on the top 6 features selected at 316. At 326, unsupervised and supervised clustering is applied based on the set of delta-QVT features, to characterize the patient as a responder or non-responder.

Example methods and apparatus demonstrably improve on conventional technologies for predicting response to immunotherapy. For example, embodiments described herein predict response to nivolumab immunotherapy with an average AUC of at least 0.79, compared with conventional approaches such as over-expression of the PDL1 biomarker which has an accuracy of only approximately 50%. By increasing the accuracy with which response to immunotherapy is predicted, example methods and apparatus produce the concrete, real-world technical effect of increasing the probability that at-risk patients receive timely treatment tailored to the particular pathology they exhibit. The additional technical effect of reducing the expenditure of resources and time on patients who have a less aggressive pathology is also achieved. Example embodiments further improve on conventional approaches by providing a more accurate second reader to facilitate the reduction of inter-reader and intra-reader variability among human radiologists or oncologists. Example methods and apparatus thus improve on conventional methods in a measurable, clinically significant way. When implemented as part of a personalized medicine system or an NSCLC response prediction system, which may include a computer or a processor configured to predict NSCLC immunotherapy response, example embodiments improve the performance of a machine, computer, or computer-related technology by providing a more accurate and more reliable prediction of NSCLC immunotherapy response compared to conventional approaches to controlling a machine to predict NSCLC immunotherapy response.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 4:
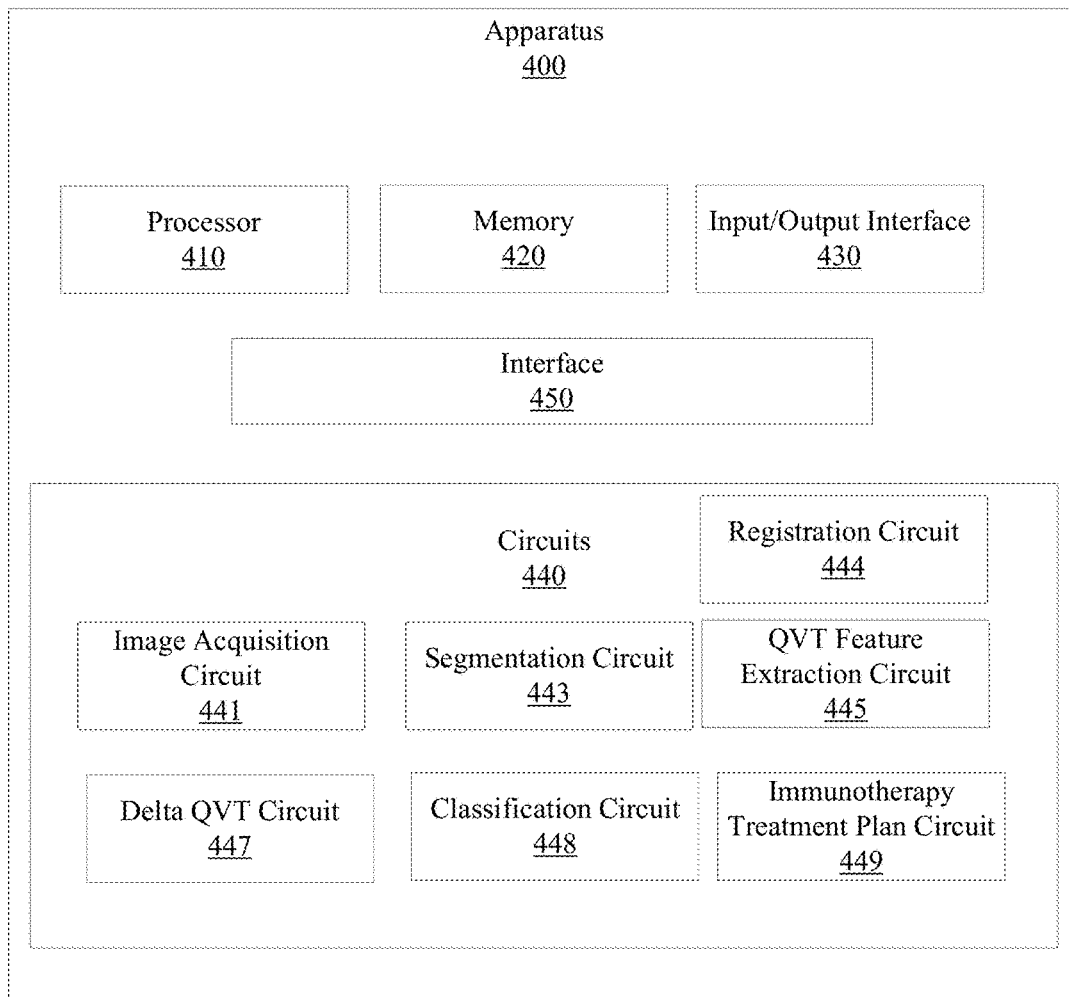
FIG. 4 illustrates an example apparatus that predicts response to immunotherapy based on serial QVT features.

FIG. 4 illustrates an example apparatus 400 that predicts patient response to immunotherapy. Apparatus 400 includes a processor 410, a memory 420, an input/output interface 430, a set of circuits 440, and an interface 450 that connects the processor 410, the memory 420, the input/output interface 430, and the set of circuits 440. The set of circuits 440 includes an image acquisition circuit 441, a segmentation circuit 443, a registration circuit 444, a QVT feature extraction circuit 445, a delta-QVT circuit 447, and a classification circuit 448.

Memory 420 is configured to store a digitized CT pre-treatment image and at least one digitized CT post-treatment image of a region of tissue demonstrating NSCLC. At least one CT pre-treatment image and a member of the at least one CT post-treatment image are of the same patient. The pre-treatment image is acquired before the patient is administered immunotherapy. The at least one CT post-treatment image is acquired at least a threshold time after the CT pre-treatment image. In one embodiment, the at least one CT post-treatment image is acquired at least two weeks after the administration of immunotherapy treatment to the patient. In another embodiment, the at least one CT post-treatment image may be acquired at a different time interval after the administration of immunotherapy. The region of tissue includes a tumor or nodule. The pre-treatment image has a plurality of voxels and the at least one post-treatment image has a plurality of voxels. A voxel has an intensity value. In other embodiments, a pre-treatment image and at least one post-treatment image may be radiological images acquired using other imaging systems, modalities, parameters, or be of other regions demonstrating other types of pathology.

Image acquisition circuit 441 is configured to access the pre-treatment image and the at least one post-treatment image. Accessing the pre-treatment image and the at least one post-treatment image includes acquiring electronic data, reading from a computer file, receiving a computer file, reading from a computer memory, or other computerized activity. Accessing the pre-treatment image and the at least one post-treatment image may include accessing a digitized CT pre-treatment image and at least one digitized CT post-treatment image of a region of tissue demonstrating NSCLC stored in memory 420. In another embodiment, accessing the pre-treatment image and the at least one post-treatment image may include accessing a network attached storage (NAS), a cloud storage system, or other type of electronic storage system. Accessing the pre-treatment image and the at least one post-treatment image may, in one embodiment, include accessing a NAS device, a cloud storage system, or other type of electronic storage system using input/output interface 430. In one embodiment, the pre-treatment image or the at least one post-treatment image is a 1 mm to 5 mm thick, no-contrast chest CT image with a pixel size of 0.7 mm center to center. Other imaging approaches or parameters may be used to generate and access the image accessed by image acquisition circuit 441.

Segmentation circuit 443 is configured to annotate the tumor represented in the pre-treatment image. Segmentation circuit 443 is further configured to annotate the tumor represented in the at least one post-treatment image. In one embodiment, segmentation circuit 443 is configured to annotate the tumor using 3D Slicer software, or using an automated segmentation approach. An automated segmentation approach may include, for example, an ensemble segmentation approach, a level set model, or a combined spectral embedding/active contour (SEAC) approach. In another embodiment, other segmentation approaches may be employed, including threshold based segmentation, deformable boundary models, active-appearance models, active shape models, graph based models including Markov random fields (MRF), min-max cut approaches, or other image segmentation approaches.

Segmentation circuit 443 is further configured to generate a 3D segmented vasculature by segmenting a vessel associated with the nodule or tumor from the nodule or tumor. Segmentation circuit 443 is configured to generate a 3D segmented vasculature associated with the nodule or tumor represented in the pre-treatment image and to generate a 3D segmented vasculature associated with the nodule or tumor represented in the at least one post-treatment image. FIG. 1 illustrates an example nodule or tumor 110 and a 3D segmented vasculature 120. In one embodiment, segmentation circuit 443 segments the vessel from the nodule or tumor using a 3D click and grow approach. The 3D click and grow approach includes, in this embodiment, identifying a plurality of seed points within a volume of interest. A member of the plurality of seed points has an intensity. The volume of interest may be in the nodule or tumor, or the volume interest may include a region associated with the nodule or tumor. For example, the volume of interest may include a spherical volume extending a threshold distance from the centroid of the nodule. The 3D click and grow approach further includes computing an intensity similarity between a first member of the plurality of seed points and a second, different member of the plurality of seed points. The 3D click and grow approach also includes growing the volume of interest using a 3D region growing approach based, at least in part, on the intensity similarity. In another embodiment, segmentation circuit 443 segments the vessel from the nodule or tumor using a different segmentation approach.

In one embodiment, the volume of interest may be defined as a function of a property of the nodule or tumor. The property of the nodule or tumor may be, for example, a diameter, a radius, a perimeter, an area, a volume, or other property of the nodule or tumor. The function may define the volume of interest as, for example, a dilation of the nodule boundary, where the dilation ratio is defined by a magnitude of an axis of the nodule. In another embodiment, the volume of interest may be defined as a disc of a threshold radius defined about the centroid of the nodule or tumor, or defined on the focal points of an elliptical representation of the nodule. In one embodiment, the volume of interest may be manually defined. Other approaches or combinations of approaches may be used to define the volume of interest.

Figure 2:
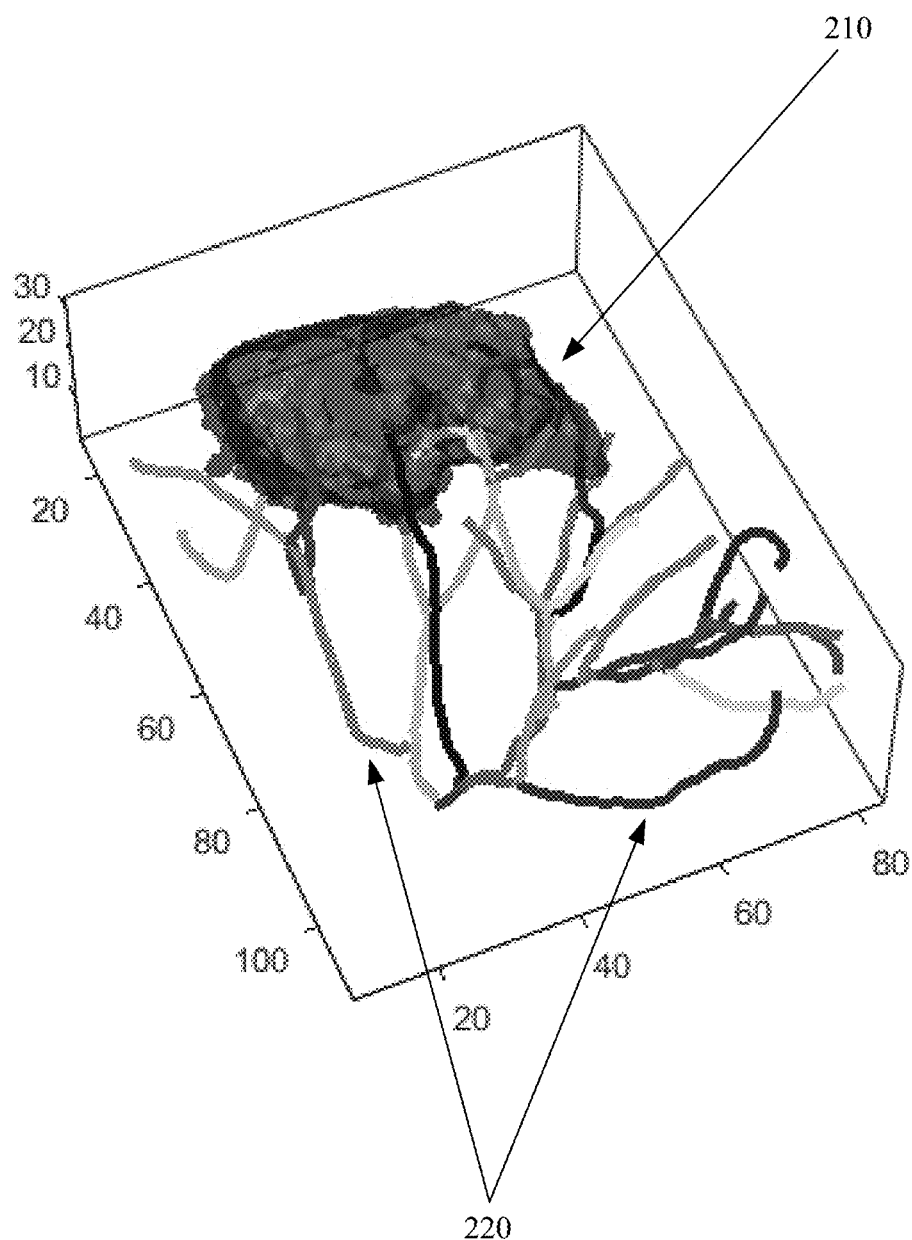
FIG. 2 illustrates an example of centerlines of an example 3D segmented vasculature.

Segmentation circuit 443 is further configured to identify a center line of the 3D segmented vasculature. In one embodiment, segmentation circuit 443 is configured to identify a center line of the 3D segmented vasculature using a fast marching approach. Segmentation circuit 443 may be configured to identify a centerline of a vessel and branching points associated with the vessel. FIG. 2 represents detected centerlines 220 associated with a nodule 210 that is similar to nodule 110. Segmentation circuit 443 is configured to identify a center line of the 3D segmented vasculature associated with the nodule or tumor represented in the pre-treatment image and to identify a center line of the 3D segmented vasculature associated with the nodule or tumor represented in the at least one post-treatment image.

Registration circuit 444 is configured to generate a registered image by registering the pre-treatment image with the at least one post-treatment image. Registration circuit 444 may register the pre-treatment image, after the tumor is annotated in the pre-treatment image and after the tumor is annotated in the at least one post-treatment image, with the at least one post-treatment image. In one embodiment, registration circuit 444 registers the pre-treatment image with the at least one post-treatment image using an affine registration approach based, at least in part, on the annotated tumors represented in the pre-treatment image and the at least one post-treatment image. In another embodiment, registration circuit 444 registers the pre-treatment image with the at least one post-treatment image using a rigid registration approach or a deformable registration approach. In another embodiment, other registration techniques may be employed.

QVT feature extraction circuit 445 is configured to select a set of pre-treatment QVT features from the registered image and to select a set of post-treatment QVT features from the registered image. In one embodiment, QVT feature extraction circuit 445 selects the set of pre-treatment QVT features and the set of post-treatment QVT features based on a threshold level of reliability and a threshold level of reproducibility associated with the QVT features. The reliability and reproducibility may be expressed as a level of stability between a pre-treatment QVT feature and its post-treatment counterpart. For example, QVT feature extraction circuit 445 may compute a level of stability between a standard deviation of torsion of a vessel segment feature extracted from the pre-treatment image and the corresponding standard deviation of torsion of a vessel segment feature extracted from the associated post-treatment image acquired of the same patient. In one embodiment, QVT feature extraction circuit 445 computes the threshold level of reliability and the threshold level of reproducibility using a concordance correlation coefficient (CCC) approach. In one embodiment, a CCC value of 0.8 is used as a threshold level of stability. In another embodiment, other, different CCC values may be employed. In another embodiment, other approaches to computing a level of stability may be employed.

In one embodiment, QVT feature extraction circuit 445 is configured to calculate the torsion for a vessel segment using a distance metric. The torsion of a vessel segment is defined as 1−(Distance/Length) where distance is the Euclidean distance of the start and end point of the segment, and where length is the number of voxels along the vessel segment. QVT feature extraction circuit 445 also extracts the curvature of a vessel segment. Curvature at a voxel of a vessel segment is proportional to the inverse of an osculating circle's radius. The osculating circle is fitted to a collection of three neighboring points along the centerline of a vessel. For a plurality of points along the center line of a vessel, QVT feature extraction circuit 445 fits a circle to compute the curvature of a specific point. QVT feature extraction circuit 445 then computes the mean and standard deviation of the curvature for points along the vessel. QVT feature extraction circuit 445 may also capture branching statistics associated with the vessel.

In one embodiment, the set of pre-treatment QVT features includes tortuosity features that describe vessels associated with the nodule or tumor. Example embodiments use a set of tortuosity features to quantify a measure of aggressiveness or irregularity in vessels associated with a nodule, tumor, or region of tissue associated with a nodule or tumor. The set of pre-treatment QVT features may include the mean of torsion of a vessel segment, or the standard deviation of torsion of a vessel segment. The set of pre-treatment QVT features may also include the mean and standard deviation of the mean curvature of a group of vessel segments. The set of pre-treatment QVT features may also include the mean and standard deviation of a vessel segment curvature and a total vessel segment length. The set of pre-treatment QVT may also include branching statistics associated with the vessel. Other tortuosity features may be extracted.

In this embodiment, the set of post-treatment QVT features includes the mean of torsion of a vessel segment, or the standard deviation of torsion of a vessel segment. The set of post-treatment QVT features may also include the mean and standard deviation of the mean curvature of a group of vessel segments. The set of post-treatment QVT features may also include the mean and standard deviation of a vessel segment curvature and a total vessel segment length. The set of post-treatment QVT may also include branching statistics associated with the vessel. In another embodiment, other QVT features may be selected, including other tortuosity or branching features. While in this embodiment three QVT features are selected, in another embodiment, other, different numbers of QVT features may be selected. For example, in one embodiment, four QVT features may be selected. In one embodiment, QVT feature extraction circuit 445 may provide the set of post-treatment QVT features or the set of pre-treatment QVT features to delta-QVT circuit 447, or memory 420.

In one embodiment, QVT feature extraction circuit 445 is further configured to normalize the set of pre-treatment QVT features and the set of post-treatment QVT features. Normalizing the set of pre-treatment QVT features and the set of post-treatment QVT features may include normalizing QVT feature values to a notionally common scale between −1 and 1.

Delta-QVT circuit 447 is configured to generate a set of delta-QVT features based on the set of pre-treatment QVT features and the set of post-treatment QVT features. Delta-QVT circuit 447 generates the set of delta-QVT features by computing a difference between the set of post-treatment radiomic features and the set of pre-treatment QVT features. Delta-QVT circuit 447 generates the set of delta-QVT features on a per-voxel basis. In one embodiment, a value for a member of the set of delta-QVT features may be computed as a percent difference PD as:

$$= \frac{\text{pre} - \text{post}}{\text{pre}} * 100,$$

where pre is a value for a pre-treatment QVT feature and post is a value for the corresponding post-treatment QVT feature. In one embodiment, the pre and post values represent the statistical measurement for the QVT feature expression calculated within a threshold proximity of a nodule. For example, the difference may be a difference in the statistical mean or standard deviation of the QVT feature value within the proximity of the nodule. The threshold proximity may be user defined, or may be a function of a property of the nodule or tumor. In another embodiment, delta-QVT circuit 447 may compute a difference between the set of post-treatment QVT features and the set of pre-treatment radiomic features using another, different technique. In another embodiment, delta-QVT circuit 447 generates the set of delta-QVT features by computing, for a threshold level of voxels (e.g., one half or one quarter of the voxels in an image), a difference between the set of post-treatment QVT features and the set of pre-treatment QVT features.

Delta-QVT circuit 447 is further configured to provide the set of delta-QVT features to classification circuit 448 or memory 420. Providing the set of delta-QVT features to the classification circuit 448 or memory 420 includes acquiring electronic data, reading from a computer file, receiving a computer file, reading from a computer memory, or other computerized activity.

Classification circuit 448 is configured to generate a probability that the region of tissue will respond to immunotherapy. Immunotherapy may include, for example, nivolumab immunotherapy, pembrolizumab immunotherapy, atezolizumab immunotherapy, or other type of immunotherapy. Classification circuit 448 computes the probability based, at least in part, on the set of delta-QVT features. Classification circuit 448 is further configured to classify the region of tissue as a responder or non-responder based, at least in part, on the probability.

In one embodiment, classification circuit 448 is configured as a machine learning classifier. The machine learning classifier may be an SVM classifier. In one embodiment, the SVM has three kernels, including a linear kernel, an RBF kernel, and a polynomial kernel. In another embodiment, the machine learning classifier is a discriminant analysis (DA) classifier, a nearest neighbor (NN) classifier, a CNN, or a random forest (RF) classifier. In this embodiment, apparatus 400 classifies a region of tissue as a responder or non-responder to nivolumab immunotherapy with an AUC of at least 0.79. In another embodiment, the probability that the region of tissue will respond to other, different types of immunotherapy may be computed.

Classification circuit 448 resolves features extracted from the digitized CT imagery at a higher order or higher level than a human can resolve in the human mind or with pencil and paper. For example, the intensity values for a voxel in a digitized CT image are not biological properties of physical lung tissue that a human eye can perceive. The QVT features provided to the machine learning classifier are of a different nature than the intensity values represented in the CT imagery. A section of lung tissue in a patient does not comprise, for example, an intensity or a standard deviation of torsion of a vessel segment feature. The probability computed by classification circuit 448 and the classification is of a different nature than the QVT features.

In one embodiment, apparatus 400 further includes an immunotherapy treatment plan circuit 449 configured to generate an NSCLC immunotherapy treatment plan for the patient represented in the pre-treatment and post-treatment image. The immunotherapy treatment plan circuit 449 generates the plan based, at least in part, on the classification and at least one of the probability, the set of delta-QVT features, the pre-treatment image, the at least one post-treatment image, or the registered image. The NSCLC immunotherapy treatment plan defines an immunotherapy agent dosage amount and an immunotherapy agent dosage schedule. Defining a personalized NSCLC immunotherapy treatment plan facilitates delivering a particular treatment that will be therapeutically active to the patient, while minimizing negative or adverse effects experienced by the patient. For example, the NSCLC immunotherapy treatment plan may define a nivolumab dosage amount and schedule for a patient identified as a responder, while for a non-responder, other treatments may be suggested. In one embodiment, the immunotherapy treatment plan circuit 449 may control an immunotherapy dosage system to administer a dosage of an immunotherapy agent defined by the NSCLC immunotherapy plan by an intravenous infusion, or by an intravesical infusion.

In another embodiment, apparatus 400 may control a computer aided diagnosis (CADx) system to classify the region of tissue represented in the pre-treatment and post-treatment imagery, based, at least in part, on the probability or the classification generated by classification circuit 448. For example, apparatus 400 may control a CADx system to predict response to immunotherapy based, at least in part, on the probability or the classification generated by classification circuit 448. In other embodiments, other types of CADx systems may be controlled, including CADx systems for predicting patient response to other types of immunotherapy or to predict response to immunotherapy in other tissue presenting other, different pathologies that may be distinguished based on features extracted by QVT feature extraction circuit 445 and differences computed by delta-QVT circuit 447 that are represented in serial CT imagery or other type of serial radiological image. For example, embodiments described herein may be employed to predict response to immunotherapy based on probabilities computed from delta-QVT features by a machine learning classifier in breast cancer (BCa), kidney disease, or brain pathologies.

Figure 5:
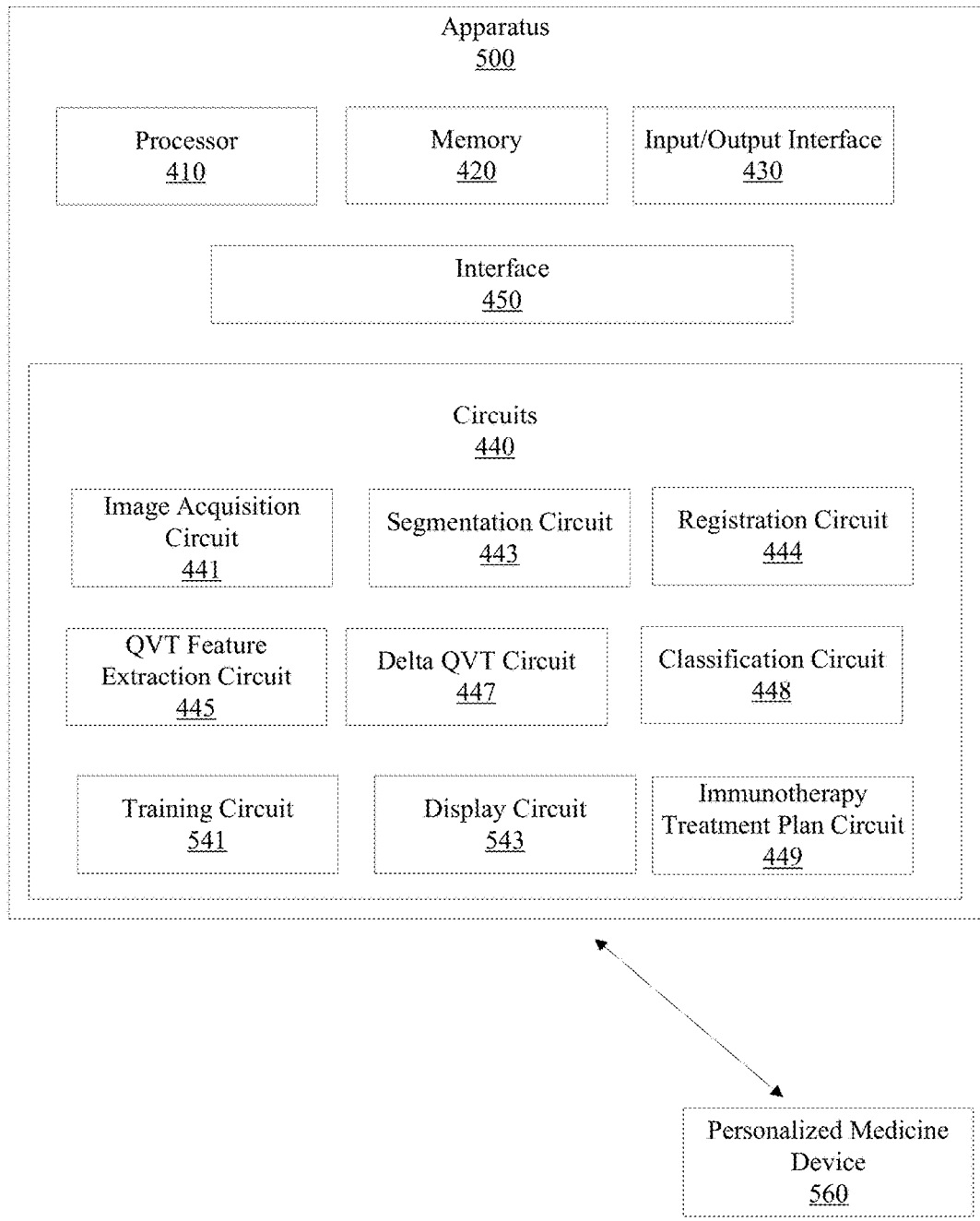
FIG. 5 illustrates an example apparatus that predicts response to immunotherapy based on serial QVT features.

FIG. 5 illustrates an apparatus 500 that is similar to apparatus 400 but that includes additional components and details. In one embodiment of apparatus 500, the set of circuits 440 further includes a training circuit 541 configured to train classification circuit 448. Training classification circuit 448 may include training the machine learning classifier. In one embodiment, the training circuit 541 accesses a dataset of CT images of a region of tissue demonstrating NSCLC. A first member of the dataset is a pre-treatment image, and a second member of the dataset is a post-treatment image of the region represented in the first member. The post-treatment image is acquired at least a threshold period of time (e.g. two weeks) after the administration of immunotherapy to the patient represented in the pre-treatment image and the post-treatment image. Training circuit 541 selects a set of training delta-QVT features from the dataset. The set of training delta-QVT images includes a feature selected from the first member, and a corresponding feature selected from the associated second member. The set of training delta-QVT features is selected based on a level of discriminability and on a level of stability. In one embodiment, the level of stability is computed using a CCC approach. QVT features that do not meet the level of stability are not selected. Training circuit 541 trains the classification circuit 448 using the set of delta-QVT features. Training circuit 541 may employ supervised or unsupervised learning to train classification circuit 448. Training circuit 541 may train the classification circuit 448 until a desired level of accuracy is achieved by classification circuit 448, until a threshold period time has been used to train classification circuit 448, until a threshold level of computational resources have be expended, until a signal instructing training circuit 541 to terminate training is received by training circuit 541, or until some other, different condition has been met.

FIG. 5 further illustrates a personalized medicine device 560. Personalized medicine device 560 may be, for example, a CADx system, an immunotherapy dosage system, or other type of personalized medicine device that may be used to facilitate the administration of immunotherapy. In one embodiment, the immunotherapy treatment plan circuit 449 may control personalized medicine device 560 to display the classification, the probability, the pre-treatment image, the post-treatment image, the registered image, the NSCLC immunotherapy treatment plan, or the set of delta-QVT features on a computer monitor, a smartphone display, a tablet display, or other displays.

In one embodiment of apparatus 500, the set of circuits 440 further includes a display circuit 543. The display circuit 543 may control the immunotherapy treatment plan circuit 449 or a CADx system to display the classification, the probability, the pre-treatment image, the post-treatment image, the registered image, the NSCLC immunotherapy treatment plan, or the set of delta-QVT features on a computer monitor, a smartphone display, a tablet display, or other displays. Displaying the classification, the probability, the pre-treatment image, the post-treatment image, the registered image, the NSCLC immunotherapy treatment plan, or the set of delta-QVT features may also include printing the classification, the probability, the pre-treatment image, the post-treatment image, the registered image, or the set of delta-QVT features. The display circuit may also control the immunotherapy treatment plan circuit 449, the classification circuit 448, or the CADx system to display operating parameters or characteristics of the machine learning classifier, during both training and testing, and during clinical operation. Displaying the classification, the probability, the pre-treatment image, the post-treatment image, the NSCLC immunotherapy treatment plan, or the set of delta-QVT features involves but is not limited to extracting and changing the character of information present in a region of tissue (e.g. biological tissue), to a radiological image (e.g. CT image), to changing the information present in the radiological image to information of a different character in the radiomic features, the probability, the characterization, and the NSCLC immunotherapy treatment plan. Embodiments described herein further transform the character of information to information suitable for display on, and display on, for example, a computer monitor, a smartphone display, a tablet display, or other displays. Thus, embodiments described herein use a combined order of specific rules, elements, or components that render information into a specific format that is then used and applied to create desired results more accurately and with greater reliability than conventional approaches: a prediction of response to immunotherapy based on a difference computed from the set of delta radiomic features.

Figure 6:
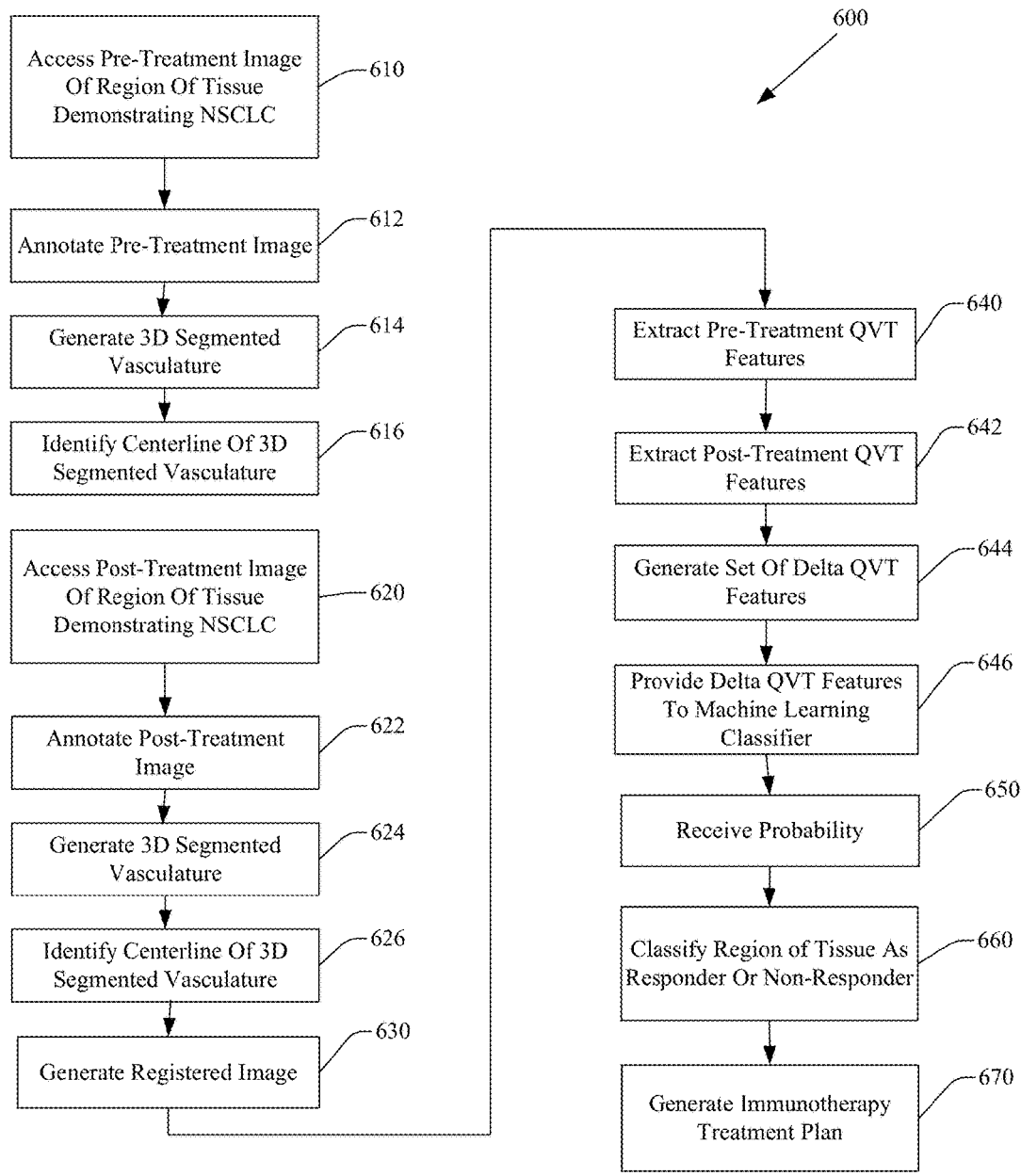
FIG. 6 illustrates an example method for predicting response to immunotherapy based on serial QVT features.

FIG. 6 illustrates a computerized method 600 for predicting NSCLC patient response to immunotherapy. Method 600 includes, at 610, accessing a pre-treatment image of a region of tissue demonstrating NSCLC. The pre-treatment image includes a representation of a tumor. The pre-treatment image includes a plurality of voxels. A voxel has an intensity value. In one embodiment, the pre-treatment image is a computed tomography (CT) image of a first patient. The pre-treatment image is acquired before the administration of immunotherapy treatment to the patient. Accessing the pre-treatment image includes acquiring electronic data, reading from a computer file, receiving a computer file, reading from a computer memory, or other computerized activity. In other embodiments, other, different types of tissue demonstrating other, different pathologies may be imaged using different imaging techniques.

Method 600 also includes, at 612, annotating the tumor represented in the pre-treatment image. Annotating the tumor represented in the pre-treatment image includes segmenting the tumor from other, non-tumor regions represented in the image.

Method 600 also includes, at 614, generating a pre-treatment 3D segmented vasculature. Method 600 generates the pre-treatment 3D segmented vasculature by segmenting a vessel associated with the tumor represented in the pre-treatment image from the tumor represented in the pre-treatment image. FIG. 1 illustrates an exemplary segmented 3D vasculature 120.

Method 600 also includes, at 616, identifying a center line of the pre-treatment 3D segmented vasculature. FIG. 2 illustrates exemplary detected centerlines 220 associated with a nodule 210.

Method 600 also includes, at 620, accessing at least one post-treatment image of the region of tissue demonstrating NSCLC. The at least one post-treatment image includes the tumor represented in the pre-treatment image. The at least one post-treatment image is acquired of the patient at least a first time interval after the pre-treatment image and after immunotherapy has been administered to the patient. In one embodiment, the first time interval is two weeks. The post-treatment image includes a plurality of voxels. A voxel has an intensity value. In one embodiment, the at least one post-treatment image is a CT image of the region of tissue represented in the pre-treatment image of the first patient. Accessing the post-treatment image includes acquiring electronic data, reading from a computer file, receiving a computer file, reading from a computer memory, or other computerized activity. In other embodiments, different types of tissue demonstrating other, different pathologies may be imaged using different imaging techniques. For example, in another embodiment, the pre-treatment image and the post-treatment image may be MRI images, combined CT/PET images, or other radiological images of NSCLC tissue or other tissue demonstrating cancerous pathology.

Method 600 also includes, at 622, annotating the tumor represented in the at least one post-treatment image. Annotating the tumor represented in the pre-treatment image or the at least one post-treatment image includes segmenting a tumor or nodule region from the background of the image. The tumor represented in the pre-treatment image or the at least one post-treatment image may be annotated using 3D Slicer software, or may be automatically segmented. Automatically segmenting the tumor may include, for example, controlling a computer or processor to use an ensemble segmentation approach, a level set model, or a combined spectral embedding/active contour (SEAC) approach to segment the tumor. In one embodiment, automatically segmenting the tumor may include, for example, controlling a computer or processor to segment the tumor using threshold based segmentation, deformable boundary models, active-appearance models, active shape models, graph based models including Markov random fields (MRF), min-max cut approaches, or other image segmentation approaches.

Method 600 also includes, at 624 generating a post-treatment 3D segmented vasculature. Method 600 generates the post-treatment 3D segmented vasculature by segmenting a vessel associated with the tumor represented in the post-treatment image from the tumor represented in the post-treatment image. Method 600 generates the post-treatment 3D segmented vasculature and the pre-treatment 3D segmented vasculature using a 3D click and grow approach. In another embodiment, method 600 generates the segmented vasculatures using another, different approach.

Method 600 also includes, at 626 identifying a center line of the post-treatment 3D segmented vasculature. Method 600 identifies a center line of the pre-treatment and post-treatment 3D segmented vasculatures using a fast marching approach. Method 600 may also identify a centerline of a vessel and branching points associated with the vessel in both the pre-treatment and post-treatment images using other, different approaches.

Method 600 also includes, at 630, generating a registered image by registering the pre-treatment image with the at least one post-treatment image. In one embodiment, registering the pre-treatment image with the at least one post-treatment image includes registering the pre-treatment image with the at least one post-treatment image using an affine registration approach. In another embodiment, the pre-treatment image may be registered with the at least one post-treatment image using a rigid registration approach, or a deformable registration approach.

Method 600 also includes, at 640 extracting a set of pre-treatment QVT features from the registered image. Method 600 also includes, at 642, extracting a set of post-treatment QVT features from the registered image. In one embodiment, the set of pre-treatment QVT features and the set of post-treatment QVT features are selected using a T-test score approach, a Wilcoxon rank sum approach, or a minimum redundancy maximum relevancy (mRMR) approach. The set of pre-treatment QVT features and the set of post-treatment QVT features may include the mean of torsion of a vessel segment, or the standard deviation of torsion of a vessel segment. The set of pre-treatment QVT features and the set of post-treatment QVT features may also include the mean and standard deviation of the mean curvature of a group of vessel segments. The set of pre-treatment QVT features and the set of post-treatment QVT features may also include the mean and standard deviation of a vessel segment curvature and a total vessel segment length. The set of pre-treatment QVT features and the set of post-treatment QVT features may also include branching statistics associated with the vessel. Other tortuosity features may be extracted. While three QVT features are extracted in this embodiment, in another embodiment, other, different numbers of radiomic features may be extracted.

In one embodiment, method 600 further includes normalizing the set of pre-treatment QVT features and the set of post-treatment QVT features. Normalizing the set of pre-treatment QVT features and the set of post-treatment QVT features may include normalizing QVT features to a notionally common scale between −1 and 1. In another embodiment, other normalization techniques may be employed.

Method 600 also includes, at 644, generating a set of delta-QVT features. Generating the set of delta-QVT features includes controlling a processor to compute, on a per-voxel basis, a difference between the set post-treatment QVT features and the set of pre-treatment QVT features. In another embodiment, delta-QVT features may be generated by computing, for a threshold number of voxels, a difference between the set post-treatment QVT features and the set of pre-treatment QVT features. The set of delta radiomic features may be selected using a concordance correlation coefficient (CCC) approach. In one embodiment, a CCC value of 0.8 is used as a threshold level of stability. In this embodiment, delta-QVT features with a CCC value of 0.8 or greater are selected. In another embodiment, other different CCC values may be employed. Different CCC values may result in different levels of stability for the set of delta-QVT features. The CCC value may be user-selected, or may be defined as a function of a desired level of stability or accuracy in predicting response to NSCLC.

Method 600 also includes, at 646, providing the set of delta-QVT features to a machine learning classifier. The machine learning classifier computes a probability that the region of tissue will respond to immunotherapy based, at least in part, on the set of delta-QVT features. In one embodiment, the machine learning classifier is a support vector machine (SVM) classifier. In one embodiment, the SVM classifier has three kernels, including a linear kernel, a radial basis function (RBF) kernel, and a polynomial kernel. In another embodiment, the machine learning classifier is a discriminant analysis (DA) classifier, a nearest neighbor (NN) classifier, a convolutional neural network, or a random forest (RF) classifier. Providing the set of delta-QVT features to the machine learning classifier may include acquiring electronic data, reading from a computer file, receiving a computer file, reading from a computer memory, or other computerized activity.

Method 600 also includes, at 650, receiving, from the machine learning classifier, the probability that the region of tissue will respond to immunotherapy. The probability is based, at least in part, on the set of delta-QVT features. Receiving the probability from the machine learning classifier may include acquiring electronic data, reading from a computer file, receiving a computer file, reading from a computer memory, or other computerized activity.

Method 600 also includes at 660, classifying the region of tissue as a responder or non-responder based, at least in part, on the probability. In one embodiment, classifying the region of tissue as a responder or non-responder may include classifying the region as a responder when the machine learning classifier provides a probability of 0.5 or greater. In another embodiment, classifying the region of tissue as a responder may be based on other probability values (e.g., 0.6, 0.7). In another embodiment, classifying the region of tissue may include categorizing the region of tissue based on more than two categories. For example, the region of tissue may be classified as one of "least likely to respond", "neutral", or "most likely to respond" based on the probability. Other categorization schemes may be employed.

In one embodiment, method 600 further includes, at 670, generating an NSCLC immunotherapy treatment plan for the patient from which the pre-treatment image and the post-treatment image were acquired. The NSCLC immunotherapy treatment plan is based, at least in part, on the classification and at least one of the probability, the set of delta-QVT features, the registered image, the pre-treatment image, or the at least one post-treatment image. In one embodiment, the NSCLC immunotherapy treatment plan defines an immunotherapy drug or agent dosage amount or an immunotherapy drug or agent dosage schedule. In one embodiment, method 600 further includes controlling a personalized medicine system or an immunotherapy dosage system to display the NSCLC immunotherapy treatment plan. In this embodiment, method 600 may include controlling the personalized medicine system or immunotherapy dosage system to display the NSCLC immunotherapy treatment plan, the classification, the probability, the set of delta-QVT features, the pre-treatment image, the at least one post-treatment image, or the registered image. In another embodiment, method 600 further includes controlling a personalized medicine system or an immunotherapy dosage system to administer a dosage of an immunotherapy agent defined by the NSCLC immunotherapy plan by intravenous infusion, by intravesical infusion, or through another, different technique.

Improved identification or classification of patients who will respond to immunotherapy may produce the technical effect of improving treatment efficacy by increasing the accuracy of and decreasing the time required to treat patients demonstrating NSCLC or other forms of cancerous pathology. Treatments and resources, including expensive immunotherapy agents, may be more accurately tailored to patients with a likelihood of benefiting from said treatments and resources, including responding to immunotherapy, so that more appropriate treatment protocols may be employed, and expensive resources are not wasted. Controlling an immunotherapy dosage system based on improved identification or classification of patients who will respond to immunotherapy further improves the operation of the immunotherapy dosage system, since unnecessary operations will not be performed.

Using a more appropriately modulated treatment may lead to less aggressive therapeutics being required for a patient or may lead to avoiding or delaying a biopsy, a resection, or other invasive procedure. When patients experiencing NSCLC who will respond to immunotherapy are more quickly and more accurately distinguished from patients who will not, patients most at risk may receive a higher proportion of scarce resources (e.g., therapeutics, physician time and attention, hospital beds) while those less likely to benefit from the treatment may be spared unnecessary treatment, which in turn spares unnecessary expenditures and resource consumption. Example methods, apparatus, and other embodiments may thus have the additional effect of improving patient outcomes compared to conventional approaches.

While FIG. 6 illustrates various actions occurring in serial, it is to be appreciated that various actions illustrated in FIG. 6 could occur substantially in parallel. By way of illustration, a first process could involve extracting QVT features from a pre-treatment CT image, a second process could involve extracting QVT features from a post-treatment CT image, and a third process could involve registering the pre-treatment CT image with the post-treatment CT image. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods described or claimed herein including method 600 and method 700. While executable instructions associated with the listed methods are described as being stored on a computer-readable storage device, it is to be appreciated that executable instructions associated with other example methods described or claimed herein may also be stored on a computer-readable storage device. In different embodiments the example methods described herein may be triggered in different ways. In one embodiment, a method may be triggered manually by a user. In another example, a method may be triggered automatically.

Figure 7:
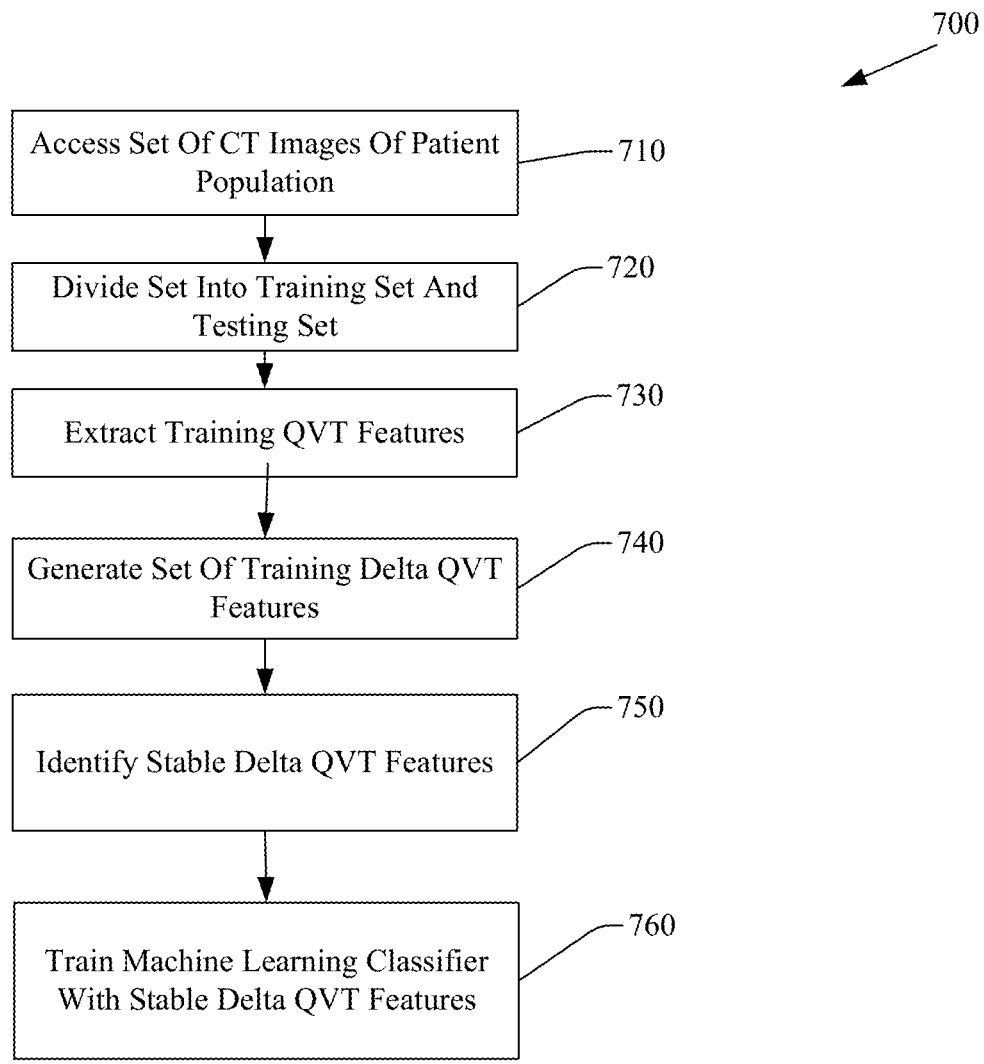
FIG. 7 illustrates an example method for training a machine learning classifier to predict response to immunotherapy based on serial QVT features.

In one embodiment, method 600 further includes training the machine learning classifier. FIG. 7 illustrates an example method 700 suitable for use by methods and apparatus described herein, including method 600 and apparatus 400 and apparatus 500, for training a machine learning classifier to predict patient response to immunotherapy. Method 700 includes, at 710, accessing a set of CT images of a population of NSCLC patients. The population of NSCLC patients includes a set of patients identified as responders to immunotherapy and a set of patients identified as non-responders to immunotherapy. A member of the set of CT images includes a representation of a tumor or nodule in the region of tissue represented in the member of the set of CT images. In one embodiment, the tumor or nodule may be annotated. In another embodiment, method 700 includes annotating the tumor using an automated segmentation approach. A member of the set of CT images includes a voxel. A voxel has an intensity. The set of CT images includes at least one pre-treatment image associated with a responder member of the population and at least one post-treatment image associated with the responder member. The set of CT images also includes at least one pre-treatment image associated with a non-responder member of the population and at least one post-treatment image associated with the non-responder member.

Method 700 also includes, at 720, dividing the set of CT images into a training set and a testing set. The training set includes at least one pre-treatment CT image and at least one post-treatment CT image associated with a responder, and at least one pre-treatment CT image and at least one post-treatment CT image associated with a non-responder. The testing set includes at least one pre-treatment CT image and at least one post-treatment CT image associated with a responder, and at least one pre-treatment CT image and at least one post-treatment CT image associated with a non-responder.

Method 700 also includes, at 730, extracting a set of training pre-treatment QVT features and a set of training post-treatment QVT features from the training set. The set of training pre-treatment QVT features and the set of training post-treatment QVT features may be extracted from the annotated tumor represented in a member of the training set, or from a region associated with the annotated tumor (e.g., a perinodular zone). In one embodiment, the set of training pre-treatment QVT features includes a maximum curvature of vessels branch feature, a standard deviation of vessel torsion feature, and a mean curvature feature. The set of training post-treatment QVT features includes a maximum curvature of vessels branch feature, a standard deviation of vessel torsion feature, and a mean curvature feature. In another embodiment, other, different QVT features may be selected. For example, other, different tortuosity or branching features may be extracted. While three QVT features are extracted for training in this embodiment, in another embodiment, other, different numbers of QVT features may be extracted. In one embodiment, the set of training pre-treatment QVT features and the set of training post-treatment QVT features are selected using a T-test score approach, a Wilcoxon rank sum approach, or a minimum redundancy maximum relevancy (mRMR) approach.

Method 700 also includes, at 740, generating a set of training delta-QVT features. The set of training delta-QVT features may be generated by computing, on a per-voxel basis, a difference between the set of training post-treatment QVT features and the set of training pre-treatment QVT features. In another embodiment, the set of training delta-QVT features may be generated by computing, for a threshold level of voxels (e.g., one half or one quarter of the voxels in an image), a difference between the set of training post-treatment QVT features and the set of training pre-treatment QVT features. In one embodiment, the difference may be a difference in the statistical mean or standard deviation of a QVT feature value over the nodule or tumor or region associated with the nodule or tumor.

Method 700 also includes, at 750, identifying a set of stable delta-QVT features in the set of training delta-QVT features. In one embodiment, the set of stable delta-QVT features are selected based on a threshold level of reliability and a threshold level of reproducibility. The set of stable delta-QVT features may be selected using a CCC approach. In one embodiment, a CCC value of 0.8 is used as a threshold level of stability. In this embodiment, delta-QVT features with a CCC value of 0.8 or greater are selected. In another embodiment, other different CCC values (e.g., 0.7, 0.9) may be employed. Other approaches to identifying the set of stable delta-QVT features may be employed.

Method 700 further includes, at 760, training the machine learning classifier using the set of stable delta radiomic features. In one embodiment, the machine learning classifier may be trained using supervised learning. In another embodiment, other machine learning training techniques may be employed. In one embodiment, method 700 further includes testing the machine learning classifier using the testing set. In one embodiment, the machine learning classifier is an SVM classifier having three kernels. The three kernels include a linear kernel, an RBF kernel, and a polynomial kernel. In another embodiment, the machine learning classifier is a DA classifier, a nearest neighbor (NN) classifier, a CNN, or a random forest (RF) classifier. Other machine learning classifiers may be employed.

Figure 8:
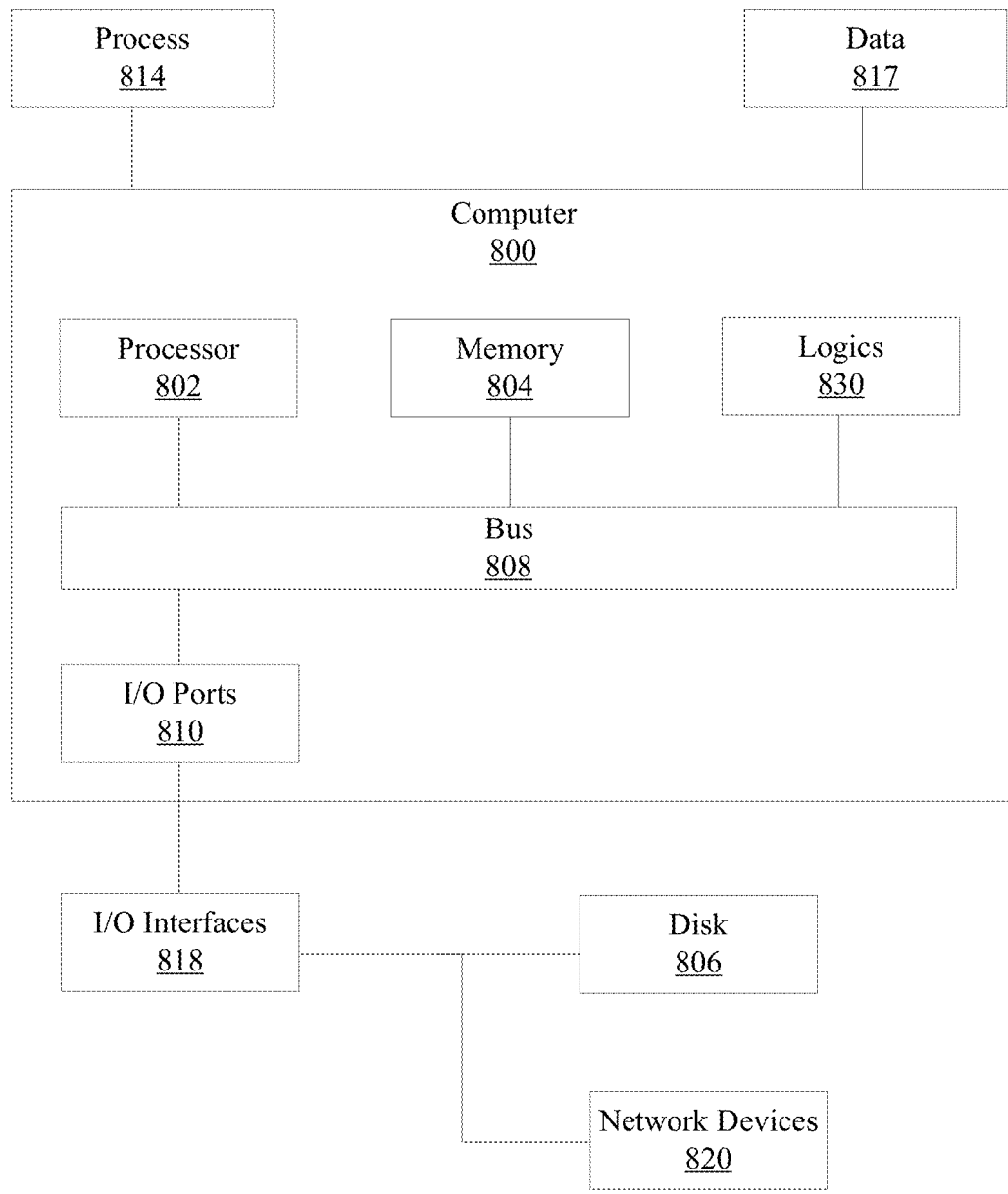
FIG. 8 illustrates an example computer in which example embodiments described herein may operate.

FIG. 8 illustrates an example computer 800 in which example methods illustrated herein can operate and in which example methods, apparatus, circuits, operations, or logics may be implemented. In different examples, computer 800 may be part of a personalized medicine system, an immunotherapy agent delivery system, a CT system, may be operably connectable to a CT system, an MRI system, a personalized medicine system, or may be part of a CADx system.

Computer 800 includes a processor 802, a memory 804, and input/output (I/O) ports 810 operably connected by a bus 808. In one example, computer 800 may include a set of logics or circuits 830 that perform a method of predicting NSCLC patient response to immunotherapy using a machine learning classifier. Thus, the set of circuits 830, whether implemented in computer 800 as hardware, firmware, software, and/or a combination thereof may provide means (e.g., hardware, firmware, circuits) for predicting patient response to immunotherapy based on delta-QVT features, and a machine learning classifier. In different examples, the set of circuits 830 may be permanently and/or removably attached to computer 800.

Processor 802 can be a variety of various processors including dual microprocessor and other multi-processor architectures. Processor 802 may be configured to perform steps of methods claimed and described herein. Memory 804 can include volatile memory and/or non-volatile memory. A disk 806 may be operably connected to computer 800 via, for example, an input/output interface (e.g., card, device) 818 and an input/output port 810. Disk 806 may include, but is not limited to, devices like a magnetic disk drive, a tape drive, a Zip drive, a flash memory card, or a memory stick. Furthermore, disk 806 may include optical drives like a CD-ROM or a digital video ROM drive (DVD ROM). Memory 804 can store processes 814 or data 817, for example. Data 817 may, in one embodiment, include digitized CT images of a region of tissue demonstrating NSCLC. Disk 806 or memory 804 can store an operating system that controls and allocates resources of computer 800.

Bus 808 can be a single internal bus interconnect architecture or other bus or mesh architectures. While a single bus is illustrated, it is to be appreciated that computer 800 may communicate with various devices, circuits, logics, and peripherals using other buses that are not illustrated (e.g., PCIE, SATA, Infiniband, 1394, USB, Ethernet).

Computer 800 may interact with input/output devices via I/O interfaces 818 and input/output ports 810. Input/output devices can include, but are not limited to, CT systems, MRI systems, digital whole slide scanners, an optical microscope, a keyboard, a microphone, a pointing and selection device, cameras, video cards, displays, disk 806, network devices 820, or other devices. Input/output ports 810 can include but are not limited to, serial ports, parallel ports, or USB ports.

Computer 800 may operate in a network environment and thus may be connected to network devices 820 via I/O interfaces 818 or I/O ports 810. Through the network devices 820, computer 800 may interact with a network. Through the network, computer 800 may be logically connected to remote computers. The networks with which computer 800 may interact include, but are not limited to, a local area network (LAN), a wide area network (WAN), or other networks, including the cloud.

Examples herein can include subject matter such as an apparatus, a personalized medicine system, a CADx system, a processor, a system, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting patient response to immunotherapy according to embodiments and examples described.

One example embodiment includes a computer-readable storage device storing computer-executable instructions that, in response to execution, cause an immunotherapy response prediction system, or a processor, to perform operations. The operations may include accessing a pre-treatment image of a region of tissue demonstrating NSCLC. The pre-treatment image represents a tumor or lung nodule located in the region of tissue. The pre-treatment image further represents a vasculature associated with the tumor or lung nodule. The pre-treatment image includes a plurality of voxels, a voxel having an intensity value.

An immunotherapy response prediction system or processor may include circuitry such as, but not limited to, one or more single-core or multi-core processors. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The operations may also include annotating the tumor represented in the pre-treatment image. In one embodiment, the tumor represented in the pre-treatment image may be annotated using 3D Slicer software, or may be annotated automatically. Annotating the tumor may include segmenting the tumor from the background of the image or from other, non-tumor tissue represented in the image. Machine learning tumor segmentation techniques may be employed.

The operations may also include accessing at least one post-treatment image of the region of tissue demonstrating NSCLC. The at least one post-treatment image represents the tumor represented in the pre-treatment image. The at least one post-treatment image further represents a vasculature associated with the tumor or lung nodule. The at least one post-treatment image includes a plurality of voxels. A voxel has an intensity value.

The operations may also include annotating the tumor represented in the at least one post-treatment image. In one embodiment, the tumor represented in the at least one post-treatment image may be annotated using 3D Slicer software, or may be annotated automatically. Annotating the tumor may include segmenting the tumor from the background of the at least one post-treatment image or from other, non-tumor tissue represented in the image. Machine learning tumor segmentation techniques may be employed.

The operations also include generating a registered image by registering the pre-treatment image with the at least one post-treatment image. In one embodiment, the registered image is generated using affine registration. In another embodiment, the operations may include other registration approaches, including a rigid registration approach, or a deformable registration approach.

In one embodiment, the operations include accessing a registered radiological image of a region of tissue demonstrating NSCLC. The registered radiological image has a plurality of voxels, a voxel having an intensity. The registered radiological image includes a pre-treatment radiological image of the region of tissue registered with a post-immunotherapy radiological image of the region of tissue. The registered radiological image includes a tumor and a vasculature associated with the tumor.

The operations also include extracting a set of pre-treatment QVT features from the registered image or the registered radiological image. In one embodiment, the set of pre-treatment QVT features includes a maximum curvature of vessels branch feature, a standard deviation of vessel torsion feature, and a mean curvature feature. In another embodiment, other, different QVT features may be selected.

The operations also include extracting a set of post-treatment QVT features from the registered image or the registered radiological image. In one embodiment, the set of post-treatment QVT features includes a maximum curvature of vessels branch feature, a standard deviation of vessel torsion feature, and a mean curvature feature. In another embodiment, other, different QVT features may be selected. While three QVT features are extracted in this embodiment, in another embodiment, other, different numbers of QVT features may be extracted. In one embodiment, the operations further include normalizing the set of pre-treatment QVT features and the set of post-treatment QVT features.

The operations also include generating a set of delta-QVT features by computing, on a per-voxel basis, a difference between the set post-treatment QVT features and the set of pre-treatment QVT features. A delta-QVT feature has a level of stability. In one embodiment, the operations further include selecting the set of delta-QVT features based, at least in part, on the level of stability of a delta-QVT feature.

The operations also include computing a probability that the region of tissue will respond to immunotherapy. Computing the probability may include, in one embodiment, providing the set of delta-QVT features to a machine learning classifier. The machine learning classifier may be an SVM, a QDA classifier, an LDA classifier, a random forests classifier, a CNN, or other type of machine learning classifier. In this embodiment, the machine learning classifier computes a probability that the region of tissue will respond to immunotherapy based, at least in part on the set of delta-QVT features. In one embodiment, the operations further include training the machine learning classifier. In one embodiment, the operations further include testing the machine learning classifier on a held-out testing dataset.

The operations also include receiving, from the machine learning classifier, the probability that the region of tissue will respond to immunotherapy. The probability is computed based, at least in part, on the set of delta-QVT features.

The operations also include classifying the region of tissue as a responder or non-responder based, at least in part, on the probability. In one embodiment, the region of tissue is classified as a responder when the probability has a value of 0.5 or greater. In another embodiment, the region of tissue is classified as a responder when the probability has another, different value. In one embodiment, the region of tissue is classified with an AUC of at least 0.79.

The operations further include generating an NSCLC immunotherapy treatment plan. The NSCLC immunotherapy treatment plan is based, at least in part, on the classification and at least one of the probability, the set of delta-QVT features, the registered image, the registered radiological image, the pre-treatment image, or the at least one post-treatment image. In one embodiment, the operations further include controlling an immunotherapy dosage system to administer a dosage of an immunotherapy agent defined by the NSCLC immunotherapy plan by an intravenous infusion, an intravesical infusion, or other technique.

In one embodiment, the operations further include controlling a personalized medicine system, a CADx system, or processor to display the NSCLC immunotherapy treatment plan, the probability, the classification, the set of delta-QVT features, the registered image, the registered radiological image, the at least one post-treatment image, or the pre-treatment image, on a computer monitor, a smartphone display, a tablet display, or other displays.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. An apparatus for predicting patient response to immunotherapy, the apparatus comprising:
   a processor;
   a memory that stores a digitized computed tomography (CT) pre-treatment image and at least one digitized CT post-treatment image of a region of tissue demonstrating non-small cell lung cancer (NSCLC), where the region of tissue includes a tumor, where the pre-treatment image includes a plurality of voxels and the at least one digitized CT post-treatment image includes a plurality of voxels;

an input/output (I/O) interface;

a set of circuits comprising an image acquisition circuit, a segmentation circuit, a registration circuit, a quantitative vessel tortuosity (QVT) feature extraction circuit, a delta-QVT circuit, and a classification circuit; and an interface to connect the processor, the memory, the I/O interface and the set of circuits;

the image acquisition circuit configured to access the pre-treatment image and the at least one digitized CT post-treatment image;

the segmentation circuit configured to:
  annotate the tumor represented in the pre-treatment image;
  annotate a three dimensional (3D) segmented vasculature associated with the tumor represented in the pre-treatment image;
  identify a center line of the 3D segmented vasculature associated with the tumor represented in the pre-treatment image;
  annotate the tumor represented in the at least one digitized CT post-treatment image;
  annotate a 3D segmented vasculature associated with the tumor represented in the at least one digitized CT post-treatment image; and
  identify a center line of the 3D segmented vasculature associated with the tumor represented in the post-treatment image;

the registration circuit configured to generate a registered image by registering the pre-treatment image with the at least one digitized CT post-treatment image;

the QVT feature extraction circuit configured to:
  select a set of pre-treatment QVT features from the registered image; and
  select a set of post-treatment QVT features from the registered image;

the delta-QVT circuit configured to:
  generate a set of delta-QVT features by computing a difference between the set of post-treatment QVT features and the set of pre-treatment QVT features; and
  provide the set of delta-QVT features to the classification circuit; and the classification circuit configured to:
  generate a probability that the region of tissue will respond to immunotherapy based, at least in part, on the set of delta-QVT features; and
  classify the region of tissue as a responder or non-responder based, at least in part, on the probability.

2. The apparatus of claim 1, where the segmentation circuit is configured to annotate the tumor represented in the pre-treatment image or the at least one digitized CT post-treatment image using an ensemble segmentation approach, a level set model, or a combined spectral embedding/active contour (SEAC) approach.

3. The apparatus of claim 1, where the segmentation circuit is configured to annotate the 3D segmented vasculature associated with the tumor represented in the pre-treatment image or the at least one digitized CT post-treatment image using a three dimensional (3D) click and grow approach.

4. The apparatus of claim 3, where the segmentation circuit is configured to annotate the 3D segmented vasculature associated with the tumor represented in the pre-treatment image or the at least one digitized CT post-treatment image using the 3D click and grow approach by:
  identifying a plurality of seed points within a volume of interest, where a member of the plurality of seed points has an intensity, where the volume of interest is in the tumor;
  computing an intensity similarity between a first member of the plurality of seed points and a second, different member of the plurality of seed points; and
  growing the volume of interest using a 3D region growing approach based, at least in part, on the intensity similarity.

5. The apparatus of claim 1, where the segmentation circuit is configured to identify the center line of the 3D segmented vasculature represented in the pre-treatment image or the at least one digitized CT post-treatment image using a fast marching approach.

6. The apparatus of claim 1, where the registration circuit registers the pre-treatment image with the at least one digitized CT post-treatment image using an affine registration approach, a rigid registration approach, or a deformable registration approach.

7. The apparatus of claim 1, where the QVT feature extraction circuit selects the set of pre-treatment QVT features and the set of post-treatment QVT features based on a threshold level of reliability and a threshold level of reproducibility, where the QVT feature extraction circuit computes the threshold level of reliability and the threshold level of reproducibility using a concordance correlation coefficient (CCC) approach.

8. The apparatus of claim 7, where the where the set of pre-treatment QVT features includes a maximum curvature of vessels branch feature, a standard deviation of vessel torsion feature, and a mean curvature feature, and where the set of post-treatment QVT features includes a maximum curvature of vessels branch feature, a standard deviation of vessel torsion feature, and a mean curvature feature.

9. The apparatus of claim 1, where the classification circuit includes a machine learning classifier, where the machine learning classifier is a support vector machine (SVM) having three kernels, where the three kernels include a linear kernel, a radial basis function (RBF) kernel, and a polynomial kernel.

10. The apparatus of claim 1, where the classification circuit includes a machine learning classifier, where the machine learning classifier is a discriminant analysis (DA) classifier, a nearest neighbor (NN) classifier, a convolutional neural network (CNN), or a random forest (RF) classifier.

11. The apparatus of claim 1, the set of circuits further comprising an immunotherapy treatment plan circuit configured to generate an NSCLC immunotherapy treatment plan based, at least in part, on the classification and at least one of the probability, the set of delta-QVT features, the pre-treatment image, or the at least one digitized CT post-treatment image, where the NSCLC immunotherapy treatment plan defines an immunotherapy drug dosage amount and an immunotherapy drug dosage schedule.

12. The apparatus of claim 11, the immunotherapy treatment plan circuit configured to provide the NSCLC immunotherapy treatment plan to a personalized medicine system or an immunotherapy administration system.

13. The apparatus of claim 1, further comprising a training circuit configured to train the classification circuit, where the training circuit is configured to:

access a dataset of CT images of a region of tissue demonstrating NSCLC, where a first member of the dataset is a pre-treatment image, and a second member of the dataset is a post-treatment image of the region represented in the first member;

select a set of training delta-QVT features from the dataset, where the set of training delta-QVT features includes a QVT feature selected from the first member, and a corresponding QVT feature selected from the second member, where the set of training delta-QVT features is selected based on a level of discriminability and on a level of stability, where the level of stability is computed using a concordance correlation coefficient (CCC) approach; and train the classification circuit using the set of delta-QVT features.

14. A non-transitory computer-readable storage device storing computer-executable instructions that when executed by a computer control the computer to perform a method for predicting non-small cell lung cancer (NSCLC) patient response to immunotherapy, the method comprising:

accessing a pre-treatment image of a region of tissue in a patient demonstrating NSCLC, where the pre-treatment image includes a plurality of voxels;

annotating a tumor represented in the pre-treatment image;

generating a pre-treatment three dimensional (3D) segmented vasculature by segmenting a vessel associated with the tumor represented in the pre-treatment image from the tumor represented in the pre-treatment image;

identifying a center line of the pre-treatment 3D segmented vasculature;

accessing at least one post-treatment image of the region of tissue demonstrating NSCLC, where the at least one post-treatment image includes the tumor, and where the post-treatment image includes a plurality of voxels;

annotating the tumor represented in the at least one post-treatment image;

generating a post-treatment 3D segmented vasculature by segmenting a vessel associated with the tumor represented in the at least one post-treatment image from the tumor represented in the at least one post-treatment image;

identifying a center line of the post-treatment 3D segmented vasculature;

generating a registered image by registering the pre-treatment image with the at least one post-treatment image;

extracting a set of pre-treatment quantitative vessel tortuosity (QVT) features from the registered image based, at least in part on the center line of the pre-treatment 3D segmented vasculature;

extracting a set of post-treatment QVT features from the registered image based, at least in part on the center line of the post-treatment 3D segmented vasculature;

generating a set of delta-QVT features by computing, on a per-voxel basis, a difference between the set post-treatment QVT features and the set of pre-treatment QVT features;

providing the set of delta-QVT features to a machine learning classifier;

receiving, from the machine learning classifier, a probability that the region of tissue will respond to immunotherapy based, at least in part, on the set of delta-QVT features;

classifying the region of tissue as a responder or non-responder based, at least in part, on the probability; and generating an NSCLC immunotherapy treatment plan based, at least in part, on the classification and at least one of the probability, the set of delta-QVT features, the pre-treatment image, the at least one post-treatment image, or the registered image.

15. The non-transitory computer-readable storage device of claim 14, where the pre-treatment image is a computed tomography (CT) image of a first patient, and where the at least one post-treatment image is a CT image of the first patient.

16. The non-transitory computer-readable storage device of claim 14, where the at least one post-treatment image is acquired at least a first time interval after administration of immunotherapy to the patient.

17. The non-transitory computer-readable storage device of claim 14, where registering the pre-treatment image with the at least one post-treatment image includes registering the pre-treatment image with the at least one post-treatment image using an affine registration approach, a rigid registration approach, or a deformable registration approach.

18. The non-transitory computer-readable storage device of claim 14, where the set of pre-treatment QVT features includes a maximum curvature of vessels branch feature, a standard deviation of vessel torsion feature, and a mean curvature feature, and where the set of post-treatment QVT features includes a maximum curvature of vessels branch feature, a standard deviation of vessel torsion feature, and a mean curvature feature.

19. The non-transitory computer-readable storage device of claim 14, where the NSCLC immunotherapy treatment plan defines an immunotherapy drug dosage amount and an immunotherapy drug dosage schedule.

20. The non-transitory computer-readable storage device of claim 19, the method further comprising:

controlling a personalized medicine system to display the NSCLC immunotherapy treatment plan, the classification, the probability, the set of delta-QVT features, the pre-treatment image, the at least one post-treatment image, or the registered image.

21. The non-transitory computer-readable storage device of claim 14, the method further comprising training the machine learning classifier.

22. The non-transitory computer-readable storage device of claim 21, where training the machine learning classifier includes:

accessing a set of CT images of a population of NSCLC patients, where the population includes a set of responders and a set of non-responders, where a member of the set of CT images includes a voxel, where the set of CT images includes at least one pre-treatment image associated with a responder member of the population and at least one post-treatment image associated with the responder member, and at least one pre-treatment image associated with a non-responder member of the population and at least one post-treatment image associated with the non-responder member;

dividing the set of CT images into a training set and a testing set, where the training set includes at least one pre-treatment CT image and at least one post-treatment CT image associated with a responder, and at least one pre-treatment CT image and at least one post-treatment CT image associated with a non-responder, and where the testing set includes at least one pre-treatment CT image and at least one post-treatment CT image associated with a responder, and at least one pre-treatment CT image and at least one post-treatment CT image associated with a non-responder;

extracting a set of training pre-treatment QVT features and a set of training post-treatment QVT features from the training set;

generating a set of training delta-QVT features by computing, on a per-voxel basis, a difference between the set of training post-treatment QVT features and the set of training pre-treatment QVT features;

identifying a set of stable delta-QVT features in the set of training delta-QVT features, where the set of stable delta-QVT features are selected based on a threshold level of reliability and a threshold level of reproducibility using a concordance correlation coefficient (CCC) approach; and training the machine learning classifier using the set of stable delta-QVT features.

23. The non-transitory computer-readable storage device of claim 22, the method further comprising testing the machine learning classifier using the testing set.

24. The non-transitory computer-readable storage device of claim 14, where the machine learning classifier is a support vector machine (SVM).

25. The non-transitory computer-readable storage device of claim 24, where the SVM has three kernels, where the three kernels include a linear kernel, a radial basis function (RBF) kernel, and a polynomial kernel.

26. The non-transitory computer-readable storage device of claim 14, where the machine learning classifier is a discriminant analysis (DA) classifier, a nearest neighbor (NN) classifier, a convolutional neural network (CNN), or a random forest (RF) classifier.

27. The non-transitory computer-readable storage device of claim 14, where the set of pre-treatment QVT features and the set of post-treatment QVT features are selected using a minimum redundancy maximum relevance (mRMR) approach, a T-test approach, or a Wilcoxon rank sum test.

28. The non-transitory computer-readable storage device of claim 14, where the set of delta-QVT features are selected based on a threshold level of reliability and a threshold level of reproducibility.

29. The non-transitory computer-readable storage device of claim 28, where the threshold level of reliability and the threshold level of reproducibility are computed using a concordance correlation coefficient (CCC) approach.

30. A computer-readable storage device storing computer-executable instructions that, in response to execution, cause an immunotherapy prediction response system to perform operations comprising:

accessing a pre-treatment radiological image of a region of tissue demonstrating non-small cell lung cancer (NSCLC), where the pre-treatment radiological image includes a tumor and a vasculature associated with the tumor, where the pre-treatment radiological image includes a plurality of voxels;

accessing at least one post-treatment radiological image of the region of tissue demonstrating NSCLC, where the at least one post-treatment radiological image includes the tumor and the vasculature, where the post-treatment radiological image includes a plurality of voxels;

generating a registered image by registering the pre-treatment radiological image with the at least one post-treatment radiological image;

extracting a set of pre-treatment quantitative vessel tortuosity (QVT) features from the vasculature represented in the registered image;

extracting a set of post-treatment QVT features from the vasculature represented in the registered image;

generating a set of delta-QVT features by computing a difference between the set of post-treatment QVT features and the set of pre-treatment QVT features, where a member of the set of delta-QVT features has a threshold level of stability;

providing the set of delta-QVT features to a machine learning classifier;

receiving, from the machine learning classifier, a probability that the region of tissue will respond to immunotherapy based, at least in part, on the set of delta-QVT features;

classifying the region of tissue as a responder or non-responder based, at least in part, on the probability; and generating an NSCLC immunotherapy treatment plan based, at least in part, on the classification and at least one of the probability, the set of delta-QVT features, the pre-treatment radiological image, or the at least one post-treatment radiological image.

31. A computer-readable storage device storing computer-executable instructions that, in response to execution, cause an immunotherapy prediction response system to perform operations comprising:

accessing a registered radiological image of a region of tissue demonstrating non-small cell lung cancer (NSCLC), where the registered radiological image includes a pre-treatment radiological image of the region of tissue registered with a post-immunotherapy radiological image of the region of tissue, where the registered radiological image includes a tumor and a vasculature associated with the tumor, where the registered radiological image includes a plurality of voxels;

extracting a set of pre-treatment quantitative vessel tortuosity (QVT) features from the vasculature represented in the registered radiological image;

extracting a set of post-treatment QVT features from the vasculature represented in the registered radiological image;

generating a set of delta-QVT features by computing a difference between the set of post-treatment QVT features and the set of pre-treatment QVT features, where a member of the set of delta-QVT features has a threshold level of stability;

computing a probability that the region of tissue will respond to immunotherapy based, at least in part, on the set of delta-QVT features;

classifying the region of tissue as a responder or non-responder based, at least in part, on the probability; and generating an NSCLC immunotherapy treatment plan based, at least in part, on the classification and at least one of the probability, the set of delta-QVT features, or the registered radiological image.

* * * * *

UNITED STATES PATENT AND TRADEMARK OFFICE
CERTIFICATE OF CORRECTION

PATENT NO. : 10,441,215 B2
APPLICATION NO. : 15/893086
DATED : October 15, 2019
INVENTOR(S) : Anant Madabhushi et al.

It is certified that error appears in the above-identified patent and that said Letters Patent is hereby corrected as shown below:

In the Specification

Column 1, Line 11; please add the following federal funding notice:
--This invention was made with government support under grants CA179327, CA195152, DK098503, CA199374, CA202752, CA208236, and RR012463 awarded by the National Institutes of Health; and grants W81XWH-16-1-0329, W81XWH-14-1-0323, W81XWH-13-1-0418, and W81XWH-15-1-0558 awarded by the Department of Defense. The government has certain rights in the invention.--

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*